US010626392B2

United States Patent
Prangenberg et al.

(10) Patent No.: US 10,626,392 B2
(45) Date of Patent: Apr. 21, 2020

(54) PARTICULATE SOLID COMPOSITE MATERIAL FOR NUCLEIC ACID PURIFICATION, CONTAINING MAGNETIC NANOPARTICLES

(71) Applicant: AXAGARIUS GMBH & CO. KG, Düren (DE)

(72) Inventors: Thomas Prangenberg, Sankt Augustin (DE); Helmut Riering, Kerpen (DE)

(73) Assignee: AXAGARIUS GMBH & CO. KG (DE)

( * ) Notice: Subject to any disclaimer, the term of this patent is extended or adjusted under 35 U.S.C. 154(b) by 0 days.

(21) Appl. No.: 15/807,029

(22) Filed: Nov. 8, 2017

(65) Prior Publication Data

US 2018/0127742 A1   May 10, 2018

(30) Foreign Application Priority Data

Nov. 9, 2016   (DE) .................. 10 2016 121 483

(51) Int. Cl.
*C08G 18/42* (2006.01)
*C08G 18/66* (2006.01)
(Continued)

(52) U.S. Cl.
CPC ............ *C12N 15/1013* (2013.01); *B03C 1/01* (2013.01); *B03C 1/32* (2013.01); *C08G 18/0823* (2013.01);
(Continued)

(58) Field of Classification Search
None
See application file for complete search history.

(56) References Cited

U.S. PATENT DOCUMENTS

| 4,267,234 A | 5/1981 | Rembaum |
| 5,648,124 A | 7/1997 | Sutor |

(Continued)

FOREIGN PATENT DOCUMENTS

| DE | 10111520 A1 | 1/2003 |
| EP | 0106873 A1 | 5/1984 |

(Continued)

OTHER PUBLICATIONS

P Popa et al. "Isocyanate Free Polyurethane Coatings for Industrial Metal Applications." http://msdssearch.dow.com/PublishedLiteratureDOWCOM/dh_0933/0901b80380933b28.pdf?filepath=coatings/pdfs/noreg/884-00796.pdf&fromPage=GetDoc, 19 pages. Accessed Nov. 19, 2018. Originally published Feb. 2015 (Year: 2015).*

(Continued)

*Primary Examiner* — Isaac Shomer
(74) *Attorney, Agent, or Firm* — Faegre Drinker Biddle & Reath LLP

(57) ABSTRACT

Particulate solid composite material for purifying nucleic acids containing magnetic nanoparticles embedded in a carrier matrix based on at least one polymer that is obtained by polyaddition of
a) at least one isocyanate-reactive monomer A, selected from compounds containing
at least two functional groups, each having at least one Zerewitinoff-reactive hydrogen atom, and
in addition to these at least two functional groups, carry at least one anionic or potentially anionic residue, preferably selected from the group consisting of carboxylate, sulfonate or combinations thereof,
with
b) at least one polyisocyanate monomer B
with the provisio that said polyaddition occurs in the presence of magnetic nanoparticles, (Continued)

is particularly suitable as carrier material for purification of nucleic acids. Said composite material is easy to prepare, is stable, and magnetic and has outstanding application properties in the bind-wash-elute purification of nucleic acids using magnetic separation.

19 Claims, 5 Drawing Sheets

(51) Int. Cl.
    *C08G 18/08*       (2006.01)
    *B03C 1/01*        (2006.01)
    *C12N 15/10*      (2006.01)
    *B03C 1/32*        (2006.01)
    *C08G 18/32*      (2006.01)
    *C08G 18/34*      (2006.01)
    *C08G 18/48*      (2006.01)
    *C08G 18/73*      (2006.01)
    *C08G 18/75*      (2006.01)
    *C08G 18/76*      (2006.01)

(52) U.S. Cl.
    CPC ..... *C08G 18/3206* (2013.01); *C08G 18/3215* (2013.01); *C08G 18/348* (2013.01); *C08G 18/4233* (2013.01); *C08G 18/4238* (2013.01); *C08G 18/4277* (2013.01); *C08G 18/48* (2013.01); *C08G 18/6677* (2013.01); *C08G 18/6681* (2013.01); *C08G 18/73* (2013.01); *C08G 18/755* (2013.01); *C08G 18/7621* (2013.01); *B03C 2201/18* (2013.01)

(56) References Cited

U.S. PATENT DOCUMENTS

| | | | |
|---|---|---|---|
| 5,705,628 A * | 1/1998 | Hawkins | ............ C12N 15/1013 252/62.51 R |
| 6,204,033 B1 | 3/2001 | Müller-Schulte | |
| 7,989,614 B2 | 8/2011 | Deggerdal et al. | |
| 8,945,509 B2 | 2/2015 | Lau et al. | |
| 2003/0175691 A1* | 9/2003 | Elaissari | ............. C07K 1/22 435/5 |
| 2005/0014001 A1* | 1/2005 | Fonnum | ................ B82Y 25/00 428/403 |
| 2005/0090732 A1* | 4/2005 | Ivkov | ..................... A61N 1/406 600/411 |
| 2006/0141045 A1* | 6/2006 | Bhatt | .................. A61K 9/1641 424/489 |

FOREIGN PATENT DOCUMENTS

| | | |
|---|---|---|
| EP | 1266385 A2 | 12/2002 |
| EP | 1404442 A1 | 4/2004 |
| EP | 2051075 A1 | 4/2009 |
| EP | 2916327 A1 | 9/2015 |
| EP | 3125276 A1 | 2/2017 |
| WO | WO-8303920 A1 | 11/1983 |
| WO | WO-9508583 A1 * | 3/1995 ......... C08G 18/0819 |
| WO | WO-9704862 A1 | 2/1997 |
| WO | WO-0171732 A2 | 9/2001 |
| WO | WO-03004150 A1 | 1/2003 |
| WO | WO-2005015216 A1 | 2/2005 |
| WO | WO-2006075185 A1 | 7/2006 |

OTHER PUBLICATIONS

MG Lu, JY Lee, MJ Shim, SW Kim. "Synthesis and Properties of Anionic Aqueous Polyurethane Dispersions." Journal of Applied Polymer Science, vol. 86, 2002, pp. 3461-3465. (Year: 2002).*

Z Zhou, US Kadam, J Irudayaraj. "One-stop genomic DNA extraction by salicylic acid-coated magnetic nanoparticles." Analytical Biochemistry, vol. 442, 2013, pp. 249-252. (Year: 2013).*

* cited by examiner

PARTICULATE SOLID COMPOSITE MATERIAL FOR NUCLEIC ACID PURIFICATION, CONTAINING MAGNETIC NANOPARTICLES

CROSS-REFERENCE TO RELATED APPLICATIONS

This application claims benefit of German Application No. 102016121483.3, filed Nov. 9, 2016, which is incorporated herein by reference in its entirety.

The invention falls within the technical field of nucleic acid purification and relates to the provision of a magnetic solid compensate material based on a polymer obtainable by polyaddition. The composite material can be used for purifying nucleic acids in aqueous media. The object of the invention is the special magnetic solid composite material, the preparation method thereof, the use of these magnetic solid compensate particles for isolating nucleic acids, and a suitable method and a kit for providing material for nucleic acid purification.

The analysis of biomolecules is an important method step in both diagnostic and in biochemical methods. The isolation and subsequent analysis of biomolecules, in particular of nucleic acids, from biological material is a multistep process. In this process, the biomolecules to be analyzed are first obtained from the biological material, such as from tissue, bacteria, cells, or viruses. The desired biomolecule must thereby first be released from the inside of the biological material during the so-called lysis. The release can, for example, be achieved by means of chaotropic reagents, surfactants, French press, heat shock, freeze-drying, shear forces, enzymes, or ultrasound.

In further steps, the released biomolecules are separated and isolated from the remaining components of the biological material. The skilled person is familiar with several methods for this purpose, such as e.g., ion exchange chromatography, affinity chromatography, or the so-called bind-wash-elute method.

A disadvantage of ion exchange chromatography or affinity chromatography as a purification method for nucleic acids as biomolecules is that during the preparation of the eluate, the eluted DNA must be laboriously desalted, concentrated, and elution agents removed before it is available for the subsequent processing or for the subsequent analyses. Moreover, chromatographic solid phases are expensive to prepare, which makes ion exchange chromatography uneconomical. In a "bind-wash-elute" method, the biomolecules from an aqueous sample are deposited onto a carrier material together with potentially contaminating substances, and a large part of the contaminating substances are removed from the deposited components of the sample by employing at least one wash solution. At the end of the process, the deposited biomolecule is unbound from the carrier material.

As is known, suitable carrier materials for the deposition of the biomolecules, in particular of the nucleic acids, are mineral carrier particles (such as, for example, quartz fibers, silicon, glass, aluminum oxide, zeolite, titanium dioxide, zirconium dioxide) and organic polymer particles.

In addition, the expert is familiar with magnetic carrier materials, so-called magnetic beads, onto which the desired biomolecule can deposit. The loaded magnetic beads can subsequently be washed with at least one wash solution. After the wash step is completed, the loaded magnetic beads can be collected by magnetic separation when a magnetic field is applied. The wash solution used for purification that contains the contaminating substances that were washed out can then be separated from the magnetic beads that are immobilized by the applied magnetic field. The contaminating substances can be removed in this way.

The expert knows a method for preparing magnetic beads on a $SiO_2$ basis with a porous surface from the published document EP 1 266 385 B1. For this purpose, ferro- or ferrimagnetic iron oxide particles with diameters ranging from 75 to 300 nm are dispersed in glyceryl or glycol and coated with $SiO_2$. The individually coated cores are then agglomerated to form larger particles. EP 2 916 327 A1 describes a similar method for producing ferrimagnetic, silanized iron oxide particles. The iron oxide particles used for this purpose have a core consisting of $Fe_3O_4$ and a coating consisting of $Fe_2O_3$. The magnetic particles are then produced in glycerol as a solvent at elevated temperatures (250° C.) and have a preferred size of 100 nm.

The printed publication WO 83/03920 A1 describes the production of spherical particles based on polystyrol and polyacrylates. Spherical polymer particles are first formed by radical-initiated suspension polymerization, and then swollen in an organic solvent under defined conditions. The swollen polymer particles are then brought into contact with a Fe(II)/Fe(III) salt solution so that the salts diffuse into the particles. The polymers are also functionalized with additional nitro-, nitroso- or amino groups so that the salts can absorb in the matrix. Addition of ammonium precipitates the salts, so that supramagnetic iron oxide particles are formed inside the polymer particles.

The printed publication WO 97/04862 A1 relates to the incorporation of magnetic colloids into spherical beads based on polyvinyl alcohols (PVA) as matrix material. The supramagnetic particles are thereby pre-dispensed in an aqueous suspension together with the polymer and brought into an apolar phase using emulsifiers. After the emulsion has formed, the polymer chains are cross-linked by addition of appropriate reagents, so that particles with a magnetic core and a polymer coating are formed. U.S. Pat. No. 4,267,234 also describes a comparable synthesis route, where magnetic beads based on polyglutar aldehyde are provided by means of a suspension polymerization.

EP 1 404 442 also discloses a synthesis route for the preparation of magnetic polymer particles by means of an aqueous emulsion. The monomers used can thereby be both metal-containing monomers and organic monomers that are soluble in the aqueous phase. The monomers are emulsed in an oil phase together with the magnetic particles used, which are also soluble in aqueous solution, so that after the polymerization step the particles are essentially uniformly distributed in the magnetic beads.

The technology used in U.S. Pat. No. 5,648,124 A employs a different kind of particle assembly. The superparamagnetic nanoparticles are deposited onto a core, preferably consisting of a polymer, through action of electrostatic interactions, and subsequently enclosed by an additional polymer layer.

The published document U.S. Pat. No. 7,989,614 B2 describes magnetic beads for nucleic acid purification that have a core provided with a polyurethane coating.

According to the published document U.S. Pat. No. 8,945,509 B2, magnetic beads are described that contain glycoconjugates bonded to the surface. To bond the glycoconjugates to the hydrophobic particle cores, hydrophilic co-polymer chains are used that are composed of functionalized acrylates, polyalkylene glycol, co-polymer chains based on methyl vinyl ether and maleic acid, or also polyurethane polyether co-polymer chains. The co-polymer chains functionalized with the glycoconjugates are bonded to the particle cores.

The printed publications WO 2005/015216 A1 and EP 2 051 075 A1 describe the coating of polymer particles with epoxides. The polymer particles contain embedded superparamagnetic crystals and functional groups on the surface.

According to the printed publication WO 2006/075185 A1, polymer particles that are porous, surface-functionalized, and contain superparamagnetic crystals are provided with a coating to reduce leaching by further reaction with a polyisocyanate and at least one diol.

It has been found that the embedded magnetic particles of the magnetic beads nevertheless often leach out of the carrier matrix during the application. The magnetic beads are less effective in the magnetic separation when a lower number of magnetic nanoparticles are present in the carrier matrix.

Moreover, the production of magnetic beads suitable for nucleic acid purification is cumbersome and should be simplified in order to increase the economic efficiency of magnetic separation.

The problem addressed by the present invention is to provide magnetic beads for nucleic acid purification with improved handling and improved performance in magnetic separation. The separated, nucleic acid-coated magnetic beads should also be suitable for use in subsequent applications, in particular in the polymerase chain reaction (PCR).

Moreover, the magnetic beads should be obtainable by a simple production method and therefore be economical. The production method should enable improved incorporation of the magnetic particles into the carrier matrix of the magnetic beads. Greater amounts of the magnetic particles should be present in the carrier matrix and should leach less out of the carrier matrix.

DETAILED DESCRIPTION OF THE INVENTION

Figure 1:
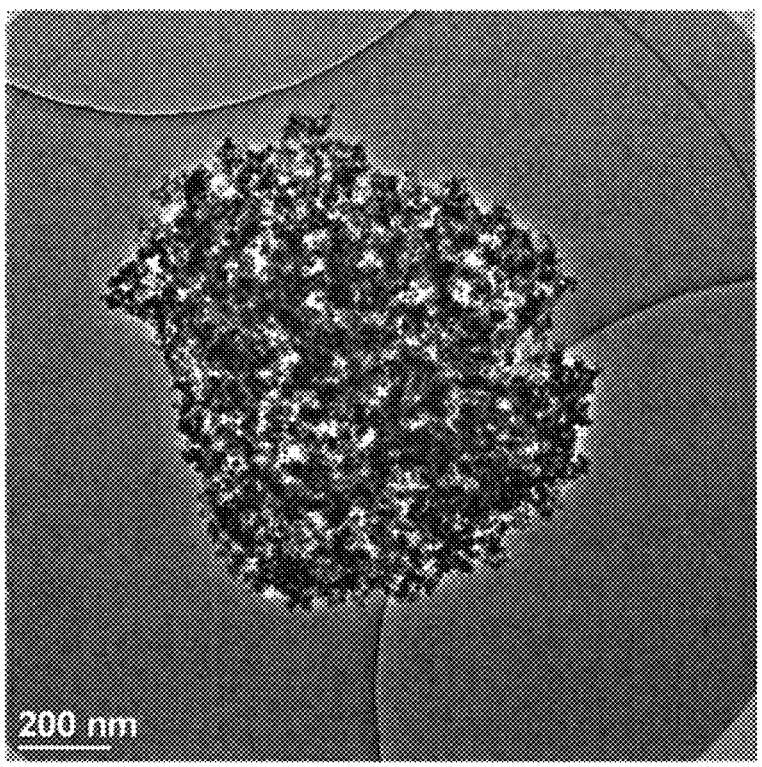
FIGS. 1 and 2 show transmission electron miscroscopic figures generated using a CM300UT FEG from FEI (formerly Philips) with 297 kV accelerating voltage and a 2 k×2 k MSC-CCD camera.

The object was solved by the particulate solid composite material for nucleic acid purification, containing magnetic nanoparticles embedded in a carrier matrix based on at least one polymer that is obtained by polyaddition of
  a) at least one isocyanate-reactive monomer A1, selected from compounds containing
    at least two functional groups each having at least one Zerewitinoff-reactive hydrogen atom, and
    in addition to these at least two functional groups carry at least one anionic or potentially anionic residue (preferably selected from the group consisting of carboxylate, sulfonate, or combinations thereof), with
  b) at least one polyisocyanate monomer B,
with the proviso that said polyaddition occurs in the presence of magnetic nanoparticles.

In the context of the present invention, the terms "magnetic beads" and "particulate solid composite material" are used synonymously.

The use of indefinite articles (a, one) or definite article (the) is—unless otherwise indicated in the individual case— not to be understood as a limiting quantity within the meaning of the present invention. What is meant—unless otherwise indicated in the individual case—is a number of at least one (i.e., one or more).

A "nanopartide" according to the invention has an average particle size (average volume) of less than 0.3 µm. Particle sizes of particulate particles were determined and analyzed using a Beckman Multisizer™ 3 Coulter Counter® (Software Beckman Coulter Multisizer™ 3, @1990-2008, Version 3.53, Oct. 15, 2008, Beckman Coulter GmbH, Krefeld).

"Magnetic" defines a substance that is magnetizable. A magnetic material should be magnetically attracted under the influence of an outer magnetic field, but after this field is removed not have a magnetic moment or hardly any magnetic moment, i.e., the substance should preferably have a remanence of almost zero or of zero so that the particles of the substance do not attract each other in the absence of an outer magnetic field and agglomerate as a result. Examples of magnetic substances are ferrimagnetic substances with a low Curie temperature or superparamagnetic substances as described, for example, in EP 0 106 873.

A "carrier matrix" is defined as particulate matter, in which particles of a solid are embedded, such as magnetic nanoparticles in the present case. The carrier matrix thereby surrounds said particles, whereby it cannot be ruled out that additional said particles are also located on the surface of the carrier matrix. Carrier matrix, magnetic nanoparticles, and optionally additional components form the particulate solid composite material according to the invention.

In the context of the present invention, "based on" means that the material the carrier matrix consists of contains more than 50 wt %, in particular more than 60 wt %, particularly preferred more than 70 wt %, more particularly preferred more than 80 wt %, most preferred more than 90 wt % of said polymer.

A "Zerewitinoff-reactive hydrogen atom" of a functionality is defined in the context of the present invention as an acidic hydrogen atom or as an "active" hydrogen atom. Such atom can be determined in a manner known per se by reaction with a corresponding Grignard reagent. The amount of Zerewitinoff-active hydrogen atoms is typically measured via methane release, which occurs according to the following reaction equation during the reaction of the substance R—XH to be tested (the functionality —XH binds to the residue on the molecule) with methyl magnesium bromide ($CH_3$—MgBr):

$$CH_3\text{—}MgBr + R\text{—}XH \rightarrow CH_4 + Mg(XR)Br$$

Zerewitinoff-active hydrogen atoms originate in particular from C—H azides of organic groups, —OH, —SH, —$NH_2$ or —NHR', where R' represents an organic residue.

An "anionic residue" according to the invention is a functionality that according to its definition differs from functionalities with Zerewitinoff-active hydrogen atoms and carries at least one anionic charge that is delocalized over at least two oxygen atoms. A "potential anionic residue" is accordingly a functionality that forms an anionic residue when the pH is changed, in particular when the pH is increased.

A chemical compound is considered "organic" when it contains at least one carbon atom and a hydrogen atom covalently bound thereto.

A particularly preferred assembly of the particulate solid composite material is present in said carrier matrix into which at least magnetic nanoparticles are embedded, whereby the material constituting the carrier matrix contains more than 50 wt %, in particular more than 60 wt %, particularly preferred more than 70 wt %, especially preferred more than 80 wt %, most preferred more than 90 wt % of said polymer.

To provide especially suitable composite materials, the preferred embodiments of the composite material according to the invention listed in the following must be considered, regardless of the previously characterized preferred assembly of the particulate solid composite material. However, it is preferred to combine at least one of the following preferred embodiments of the composite material with the aforementioned preferred or particularly preferred assembly of the particulate solid composite material.

The particles of the inventive particulate solid composite material preferably have an average particle size (average volume) of from 0.5 μm 250 μm, in particular of from 0.6 to 30 μm, particularly preferably of from 0.6 μm to 10 μm.

The embedded magnetic nanoparticles have a preferred upper limit of an average particle size (average volume) of at most 200 nm, preferably of at most 100 nm, particularly preferably of at most 50 nm.

The magnetic nanoparticles have a preferred lower limit of an average particle size (average volume) of at least 1 nm, in particular of at least 5 nm. Particularly preferred magnetic nanoparticles have an average particle size (average volume) within the range of a combination of previously defined upper and lower limits.

The magnetic nanoparticles contained are preferably selected from ferromagnetic nanoparticles, ferrimagnetic nanoparticles, superparamagnetic nanoparticles or mixtures thereof, preferably from superparamagnetic nanoparticles. Superparamagnetic particles can be synthesized using conventional methods, such as those described e.g., in J.-C.

Bacri, R. Perzynski, D. Salin, V. Cabuil, R. Massart, Ionic Ferrofluids: A crossing of chemistry and physics, J. Magn. Magn. Mater., 1990, 85, 27-32.

Metalloxides are preferably suitable as magnetic nanoparticles; particularly preferable are iron oxides such as $Fe_3O_4$ or $Fe_2O_3$. It is thereby possible that some or all of the divalent iron atoms are substituted with a divalent metal that is different from iron, such as in particular chromium, cobalt, copper, magnesium, manganese, nickel, vanadium and/or tin. It is particularly preferred if the magnetic nanoparticles contains comprise iron oxide, in particular magnetite, maghemite or mixtures thereof. Such particles are, for example, commercially available under the name Bayoxide® or can be produced as described in the Examples (see below).

The magnetic nanoparticles are contained in said composite material preferably in an amount of at least 40 wt %, particularly preferred in an amount of at least 50 wt %, more particularly preferred in an amount of at least 60 wt %, most preferred of at least 75 wt %, relative to the total weight of the inventive composite material.

The magnetic nanoparticles can be surface-modified with organic compounds having a number average molecular weight Mn of less than 1000 g/mol and carrying at least one anionic or potentially anionic residue. To realize this embodiment, onto the surface of the magnetic nanoparticles are preferably deposited hydroxy carboxylic acids, particularly preferably monohydroxy-$(C_3-C_{10})$ carboxylic acids, in particular citric acid, 2-hydroxysuccinic acid, glycolic acid, 2-hydroxypropanoic acid, 3-hydroxypropanoic acid, 2-hydroxy-2-methylpropanoic acid, 2-hydroxybutanoic acid, 3-hydroxybutanoic acid, 4-hydroxybutanoic acid, 2-hydroxybutanedioic acid 2-Hydroxypentanoic acid, 3-hydroxypentanoic acid, 4-hydroxypentanoic acid, 5-hydroxypentanoic acid, 2-hydroxypentanedioic acid, 3-hydroxypentanedioic acid, 3-carboxy-3-hydroxypentanedioic acid, 2-hydroxyhexanioc acid, 3-hydroxyhexanoic acid, 4-hydroxyhexanoic acid, 5-hydroxyhexanoic acid, 6-hydroxyhexanoic acid, 2-hydroxy-1,6-hexanedioic acid, 3-hydroxy-1,6-hexanedioic acid, 3-carboxy-2-hydroxy-1,6-hexanedioic acid, 3-carboxy-3-hydroxy-1,6-hexanedioic acid, 3-carboxy-3-hydroxy-1,6-hexanedioic acid, 2-carboxy-4-hydroxy-1,6-hexanedioic acid or combination thereof. A surface-modified magnetic nanoparticle is also a nanoparticle within the meaning of the aforementioned definition.

The isocyanate-reactive monomer A1 suitable for the polyaddition is in particular a compound comprising
  at least two functional groups, each carrying at least one Zerewitinoff-reactive hydrogen atom, independently selected from the group consisting of hydroxyl, primary amine, secondary amine, thiol, ketimine, ketazine, oxazolidine and
  in addition to these at least two functional groups, at least one anionic or potentially anionic residue (preferably selected from the group consisting of carboxylate, sulfonate or combinations thereof).

It is turn thereby preferred if the at least two functional groups each carrying at least one Zerewitinoff-reactive hydrogen atom are selected independently from one another from the group consisting of hydroxyl, primary amine, secondary amine.

Diols or polyols with at least one anionic or potentially anionic residue (preferably selected from the group consisting of carboxylate, sulfonate, or combinations thereof) are preferably used as isocyanate-reactive monomer A1. Particularly preferred diols are those of the general formula HO—R—OH with R=aliphatic, cycloaliphatic, aromatic or araliphatic residue to which at least one anionic or potentially anionic residue can respectively bind.

As used in this application, the term "aliphatic" is understood as meaning optionally substituted, linear or branched alkyl, alkenyl and alkinyl groups in which nonadjacent methylene groups (—$CH_2$—) can be substituted with hetero atoms, such as in particular with oxygen and sulfur, or with secondary amino groups.

As used in this application, the term "cycloaliphatic" shall stand for optionally substituted, carbocyclic, or heterocyclic compounds that do not belong to aromatic compounds.

As isocyanate-reaktive monomer A1 preferably one diol is selected according to the invention which is structurally derived from 1,2-propanediol, 1,3-propanediol, 2,2-bis(hydroxymethyl)propane, 1,3-butanediol, 1,4-butanediol, 1,5-pentanediol, 1,6-hexanediol, 1,8-octanediol, 1,12-dodecanediol, neopentylglycol, 1,4-bis-(hydroxymethyl)cyclohexane, 1,3-bis-(hydroxymethyl)cyclohexane, 1,2-bis-(hydroxymethyl)cyclohexane, 2-methyl-1,3-propanediol or 2-methyl-2,4-pentanediol, 2-ethyl-2-butylpropanediol, trimethylpentanediol, 2,2,4-trimethyl-1,3-pentanediol, 1,2-cyclohexanediol, 1,4-cyclohexanediol, 2,2-bis(4-hydroxycyclohexyl)propane, resorcinol, 1,2-dihydroxybenzol, with the proviso that in each case at least one anionic or potentially anionic residue (preferably selected from the group consisting of carboxylate, sulfonate, or combinations thereof) is additionally present in the molecule.

A particularly preferred isocyanate-reactive monomer A1 according to the invention is selected from 2,2-bis(hydroxymethyl)propionic acid, 2,3-diaminobenzoic acid, 2,4- diaminobenzoic acid, 2,5-diaminobenzoic acid, 2,6-diaminobenzoic acid, 3,4-diaminobenzoic acid, 3,5-diaminobenzoic acid, 2,2-bis(hydroxymethyl)acetic acid, 2,2,2-tri(hydroxymethyl)acetic acid, 2,2-bis(hydroxymethyl)propionic acid, 2,2-bis(hydroxymethyl)butyric acid, 2,2-bis(hydroxymethyl)pentanoic acid, 2,5-dihydroxy-3-methylpentanoic acid, 3,5-dihydroxy-3-methylpentanoic acid, 4,5-dihydroxy-3-methylpentanoic acid, 3,4-dihydroxy-3-methylpentanoic acid, 2,3-dihydroxy-3-methylpentanoic acid, 2,4-dihydroxy-3-methylpentanoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 2,3-dihydroxysuccinic acid, 2,5-diaminopentanoic acid, 3,5-diaminopentanoic acid, 4,5-diaminopentanoic acid, 2,3-dihydroxybenzenesulfonic acid, 3,4-dihydroxybenzenesulfonic acid, 2,4-dihydroxybenzenelsulfonic acid, 2,5-dihydroxybenzene sulfonic acid, 3,5-dihydroxybenzenesulfonic acid, 2,3-diaminobenzenesulfonic acid, 3,4-diaminobenzenesulfonic acid, 2,4-diaminobenzenesulfonic acid, 2,5-diaminobenzenesulfonic acid, 3,5-diaminobenzenesulfonic acid, 3,4-dihydroxy-2-toluenesulfonic acid, 3,4-xiamino-2-toluenesulfonic acid, 4,5-dihydroxy-2-toluenesulfonic acid, 4,5-diamino-2-toluenesulfonic acid, 5,6-dihydroxy-2-toluenesulfonic acid, 5,6-diamino-2-toluenesulfonic acid, 3,5-dihydroxy-2-toluenesulfonic acid, 3,5-diamino-2-toluenesulfonic acid, 3,6-dihydroxy-2-toluenesulfonic acid, 3,6-diamino-2-toluenesulfonic acid, 4,6-dihydroxy-2-Ttoluenesulfonic acid, 4,6-diamino-2-toluenesulfonic acid, 2,4-dihydroxy-3-toluenesulfonic acid, 2,4-diamino-3-toluenesulfonic acid, 2,5-dihydroxy-3-toluenesulfonic acid, 2,5-diamino-3-toluenesulfonic acid, 2,6-dihydroxy-3-toluenesulfonic acid, 2,6-diamino-3-toluenesulfonic acid, 4,5-dihydroxy-3-toluenesulfonic acid, 4,5-diamino-3-toluenesulfonic acid, 4,6-dihydroxy-3-toluenesulfonic acid, 4,6-dDiamino-3-toluenesulfonic acid, 5,6-dihydroxy-3-toluenesulfonic acid, 5,6-diamino-3-toluenesulfonic acid, 2,3-dihydroxy-4-toluenesulfonic acid, 2,3-diamino-4-toluenesulfonic acid, 2,5-dihydroxy-4-toluenesulfonic acid, 2,5-diamino-4-toluenesulfonic acid, 2,6-dihydroxy-4-toluenesulfonic acid, 2,6-diamino-4-Ttoluenesulfonic acid, 3,5-dihydroxy-4-toluenesulfonic acid, 3,5-diamino-4-toluenesulfonic acid, 3,6-dihydroxy-4-toluenesulfonic acid, 3,6-diamino-4-toluenesulfonic acid, 5,6-dihydroxy-4-toluenesulfonic acid, 5,6-diamino-4-toluenesulfonic acid or mixtures of at least two these compounds.

It is inventively preferred if in addition to the isocyanate-reactive monomer A1 at least one isocyanate-reactive monomer A2 is used in addition to prepare said polymer of the carrier matrix, which is selected from non-ionic compounds containing at least two functional groups, each carrying at least one Zerewitinoff-reactive hydrogen atom.

Particularly preferably, at least one isocyanate-reactive monomer A2 is selected from organic polyol, organic polyether polyol, organic polyester polyol, polycarbonate polyol, organic polyetherester carbonate polyol, organic amino alcohol, organic polyamine, organic polyalkyleneamine, or combinations thereof, more particularly preferably selected from organic diol, organic diamine, organic polyalkylene glycol, organic polyether diol, organic polyesterdiol, polycarbonate diol, polyetherestercarbonate diol, or combinations thereof.

Preferred organic dials are selected from organic polyether diols, $C_2$-$C_6$-alkane diols, (ethylenglycol, 1,2-propanediol, 1,3-propanediol, 1,3-butanediol, 1,4-butanediol, 1,5-pentanediol, 1,6-hexanediol, 1,8-octanediol, 1,12-dodecanediol, neopentylglycol, 1,4-bis-(hydroxymethyl)cyclohexane, 1,3-bis-(hydroxymethyl)cyclohexane, 1,2-bis-(hydroxymethyl)cyclohexane, 2-methy-1,3-propanediol, 2-methyl-2,4-pentanediol, 2-ethyl-2-butylpropanediol, trimethylpentanediol, 2,2,4-trimethyl-1,3-pentanediol, 1,2-cyclohexanediol, 1,4-cyclohexanediol, 2,2-bis(4-hydroxycyclohexyl)propane, 1,3-dihydroxyacetone, dihydroxyacetone dimer, or combinations of at least two of the aforementioned compounds.

Preferred polyetherdiols are in turn selected from diethylene glycol, triethylene glycol, tetraethylene glycol, polyethylene glycol, dipropylene glycol, tripropylene glycol, tetrapropylene glycol, polypropylene glycol, dibutylene glycol, tributylene glycol, tetrabutylene glycol, polybutylene glycol, or combinations of at least two of the aforementioned compounds.

Preferred suitable polyesterpolyols are selected from poly[di(ethylene glycol)adipate], polycaprolactonediol, polyethylene terephthalate, polypropylene terephthalate, polybutylene terephthalate, polyethylene isophthalate, polypropylene isophthalate, polybutylene isophthalate, polyethylene-1,4-cyclohexylene dimethylene terephthalate, polytetramethylene ether glycol terephthalate, or combinations of at least two of the aforementioned compounds.

Examples of organic polyamines suitable as monomers A2 are ethylenediamine, 1,3-diaminopropane, 1,4-diaminobutane, pentamethylenediamine, hexamethylenediamine, diethylentriamine, dipropylenetriamine, isophorondiamine, 1,4-cyclohexyldiamine, piperazine, or polyethyleneimine. Said amine compounds can also be used in blocked form, in particular as ketimines, ketazines, oxazolidines, or as ammonium salts.

It was shown to be particularly suitable if the isocyanate-reactive monomer A2 has a number average molecular weight $M_n$ of from 200 g/mol to 10,000 g/mol (preferably of from 400 g/mol to 2,500 g/mol).

In the context of the present invention, the number average molecular weight $M_n$ is determined by gel permeation chromatography (GPC) in tetrahydrofuran at 23° C., unless otherwise specified. The procedure is performed according to DIN 55672-1: "Gel permeation chromatography, part 1, tetrahydrofuran as eluent (SECurity GPC-System from PSS Polymer Service, flow rate 1.0 ml/min; columns: 2×PSS SDV linear M, 8×300 mm, 5 µm; RID detector). Polystyrene samples with known mol masses are thereby used for calibration. The calculation of the number average molecular weight is performed with software support. The baseline points and analysis limits are determined according to DIN 55672-1:2016-03 that was valid at the application date of this patent application.

Particularly preferably, monomer A2 is selected from organic polyetherpolyols, organic polyester polyols, organic polycarbonate polyols, organic polyether ester carbonate polyols, polyhydroxy olefines, or combinations of at least two compounds thereof.

More preferably, the isocyanate-reactive monomer A2 has a number average molecular weight $M_n$ of from 200 g/mol to 10,000 g/mol (preferably of from 400 g/mol to 2,500 g/mol) and is selected from organic polyalkylene glycols, organic polyether diols, organic polyester diols or combinations thereof.

The composite particles according to the invention produced from said isocyanate-reactive monomers A2 having the aforementioned molecular weight have good elasticity and a particularly good embedding efficiency for magnetic nanoparticles.

It is inventively preferred if as isocyanate-reactive monomer A2 used for the polyaddition to prepare said polymer of the carrier matrix at least one first isocyanate-reactive monomer A2a is used having two functional groups, each carrying at least one Zerewitinoff reactive hydrogen atom, that are independently of one another selected from groups consisting of hydroxyl, amino, thiol, ketimine, ketazine, oxazolidine, or combinations thereof
and
at least one second isocyanate-reactive monomer A2b having more than two functional groups (preferably three functional groups) each carrying at least one Zerewitinoff-reactive hydrogen atom, are independently of one another selected from groups consisting of hydroxyl, amino, thiol, ketimine, ketazine, oxazolidine, or combinations thereof.

The isocyanate-reactive monomer A2a is thereby in turn selected according to the above provisio from organic polyetherpolyols, organic polyester polyols, organic polycarbonate polyols, organic polyether ester carbonate polyols, polyhydroxy olefines, or combinations of at least two compounds thereof.

According to the above provisio, the aforementioned organic polyether polyols, organic polyester polyols, organic polycarbonate polyols, organic polyether ester carbonate polyols, polyhydroxy olefines are also preferred for the monomer A2.

More particularly preferred the isocyanate-reactive monomer A2a has a number average molecular weight Mn of from 200 g/mol to 10,000 g/mol (preferably of from 400 g/mol to 2,500 g/mol) and is selected from organic polyalkylene glycols, organic polyether diols, organic polyester diols or combinations thereof.

At least one alcohol having three hydroxyl groups is used as the preferred isocyanate-reactive monomer A2 or A2b, in particular 1,3,5-trihydroxybenzene, 1,2,3-trihydroxybenzene, 1,2,4-trihydroxybenzene, 1,2,5-trihydroxybenzene, 1,3,4-trihydroxybenzene,
1,2,3-propanetriol, 1,1,1-propanetriol, 1,1,2-propanetriol, 1,1,3-propanetriol, 1,2,2-propanetriol, 1,1,2-ethanetriol, 1,2,3-butanetriol, 1,2,4-butanetriol, 1,2,3-pentanetriol, 1,2,4-pentanetriol, 1,2,5-pentanetriol, 1,2,3-pentanetriol, 2,3,4-pentanetriol, 1,3,5-pentanetriol, 2-methyl-1,2,4-butanetriol, 2-methyl-1,2,3-butanetriol, 2-methyl-1,1,4-butanetriol, 1,2,3-hexanetriol, 1,2,4-hexanetriol,
1,2,5-hexanetriol, 1,2,6-hexanetriol, 1,3,4-hexanetiol, 1,3,5-hexanetriol, 1,3,6-hexanetriol, 1,1,6-hexanetriol, 1,2,3-cyclohexanetriol, 1,2,4-cyclohexanetriol, 1,2,5-cyclohexanetriol, 1,1,2-cyclohexanetriol, 1,1,3-cyclohexanetriol, 1,1,4-cyclohexanetriol, 1,3,5-cyclohexanetriol,
or combinations thereof. It is particularly preferred that monomer A2b is selected in particular from 1,3,5-trihydroxybenzene, 1,2,3-propanetriol or combinations thereof.

Aromatic, araliphatic, aliphatic or cycloaliphatic polyisocyanates each with a NCO functionality ≥2 are suitable polyisocyanate monomers B. The NCO functionality in the polyisocyanate monomer B can also be present as a so-called capped NCO functionality. These are e.g., urea, biurets, allophanates, uretdiones, isocyanurates, carbodiimides.

Compounds having both an aryl residue and an aliphatic molecule fragment bonded to the aryl residue are understood as being "araliphatic." Polyisocyanates having an araliphatic molecule fragment, whereby at least one isocyanate functionality binds to the aliphatic portion of the araliphatic molecule fragment, are understood as being "araliphatic polyisocyanates."

Diisocyanates suitable as polyisocyanate monomer B are any diisocyanates accessible to phosgenation or phosgen-free methods, for example thermal urethane cleavage, the isocyanate groups of which are either bonded via optionally branched aliphatic residues or bonded to an optionally further substituted aromatic. Preferably diisocyanates of the general formula (I)

$$O=C=N-R-N=C=O \qquad (I)$$

are used, wherein R represents a cycloaliphatic ($C_{3-15}$) hydrocarbon residue, aromatic ($C_{6-15}$) hydrocarbon residue, araliphatic ($C_{6-18}$) hydrocarbon residue, or aliphatic ($C_{3-15}$) hydrocarbon residue.

A preferred polyisocyanate monomer is selected from 1,2-ethanediisocyanate, 1,3-propanediisocyanate, 1,4-butanediisocyanate, 1,5-pentanediisocyanate (PDI), 1,6-hexanediisocyanate (hexamethylene diisocyanate, HDI), 4-isocyanatomethyl-1,8-octanediisocyanate (triisocyanatononane, TIN), 4,4'-methylenebis (cyclohexylisocyanate), 3,5,5-trimethyl-1-isocyanato-3-isocyanatomethylcyclohexane (isophorone diisocyanate, IPDI), 2,4- and/or 2,6-methylcyclohexyl diisocyanate ($H_6$TDI) and ω,ω'-1,3-dimethylcyclohexanediisocyanate ($H_6$XDI), 4,'4'-diisocyanatodicyclohexyl methane, tetramethylene diisocyanate, 2-methylpentamethylene diisocyanate, 2,2,4-trimethylhexamethylene diisocyanate (THDI), dodecamethylene diisocyanate, 1,4-diisocyanatocyclohexane, 4,4'-diisocyanato-3,3'-dimethyldicyclohexylmethane, 2,2-bis(4-isocyanatocyclohexyl)-propane, 3-isocyanatomethyl-1-methyl-1-isocyanatocyclohexane (MCI), 1,3-diisooctylcyanato-4-methylcyclohexane, 1,3-diisocyanato-2-methyl cyclohexane, 2,4-toluenediisocyanate, 2,6-toluene diisocyanate, methylenediphenyl diisocyanate (MDI), naphthyldiisocyanate (NDI), 1,3-bis(isocyanatomethyl) benzene (m-xylylene diisocyanate, m-XDI), 1,4-bis(isocyanatomethyl) benzene (p-xylylene diisocyanate, p-XDI), 1,3-bis(2-isocyanatopropan-2-yl) benzene (m-tetramethylxylylene diisocyanate, m-TMXDI), 1,4-bis(2-isocyanatopropan-2-yl) benzene (p-tetramethylxylylene diisocyanate, p-TMXDI), and any mixtures of at least two of these diisocyanates.

Dimers of the aforementioned diisocyanates, trimers of the aforementioned diisocyanates or combinations thereof are also suitable.

The polyisocyanate monomer B is particularly preferably at least a cyclic polyisocyanate, in particular at least a compound of formula (I), wherein R represents a cycloaliphatic ($C_{3-15}$) hydrocarbon residue, aromatic ($C_{6-15}$) hydrocarbon residue, araliphatic ($C_{6-18}$) hydrocarbon residue. The use of cyclic polyisocyanates reduces the adsorption of the inventive composite material onto surfaces, such as e.g., vascular walls. Particles of composite material obtainable from a cyclic polyisocyanate can be readily suspended in an aqueous medium and are easy to handle during the synthesis and in the application, such as e.g., in purification methods for nucleic acids.

At least one polyisocyanate is preferably used as polyisocyanate monomer B that is selected from toluene-2,4-diisocyanate, toluene-2,6-diisocyanate, isophorone diisocyanate, and any mixtures of at least two of these diisocyanates.

In one particularly preferred embodiment, said polymer is obtained by polyaddition of at least one of the following monomer combinations, whereby the respective monomer combination listed in the row of Table 1 comprises at least monomers A1, A2a, A2b and B.

TABLE 1

| A1 | A2a | A2b | B |
|---|---|---|---|
| 2,2-Bis(hydroxymethyl) propionic acid | Polyalkylene glycol with a number average molecular weight Mn of from 200 g/mol to 10,000 g/mol (preferably of from 400 g/mol to 2,500 g/mol) | 1,3,5-Trihydroxybenzene | Toluene-2,4-diisocyanate |
| 2,2-bis(hydroxymethyl) propionic acid | Polyalkylene glycol with an number average molecular weight Mn of from 200 g/mol to 10,000 g/mol (preferably of from 400 g/mol to 2,500 g/mol) | Glycerol | Toluene-2,4-diisocyanate |
| 2,2-bis(hydroxymethyl) propionic acid | Polyalkylene glycol with an number average molecular weight Mn of from 200 g/mol to 10,000 g/mol (preferably of from 400 g/mol to 2,500 g/mol) | 1,3,5-Trihydroxybenzene | Toluene-2,4-diisocyanate and toluene-2,6-diisocyanate |
| 2,2-bis(hydroxymethyl) propionic acid | Polyalkylene glycol with an number average molecular weight Mn of from 200 g/mol to 10,000 g/mol (preferably of from 400 g/mol to 2,500 g/mol) | Glycerol | Toluene-2,4-diisocyanate and toluene-2,6-diisocyanate |
| 2,2-bis(hydroxymethyl) propionic acid | Polyethylene glycol with an number average | 1,3,5-Trihydroxybenzene | Toluene-2,4-diisocyanate 2,6-diisocyanate |
| 2,2-bis(hydroxymethyl) propionic acid | Poly[di(ethylene glycol)adipate] | 1,3,5-Trihydroxybenzene | Toluene-2,4-diisocyanate |
| 2,2-bis(hydroxymethyl) propionic acid | Poly[di(ethylene glycol)adipate] | Glycerol | Toluene-2,4-diisocyanate |
| 2,2-bis(hydroxymethyl) propionic acid | Poly[di(ethylene glycol)adipate] | 1,3,5-Trihydroxybenzene | Toluene-2,4-diisocyanate and toluene-2,6-diisocyanate |
| 2,2-bis(hydroxymethyl) propionic acid | Poly[di(ethylene glycol)adipate] | Glycerol | Toluene-2,4-diisocyanate and toluene-2,6-diisocyanate |
| 2,2-bis(hydroxymethyl) propionic acid | ($C_2$-$C_6$)-alkanediol | 1,3,5-Trihydroxybenzene | Toluene-2,4-diisocyanate |
| 2,2-bis(hydroxymethyl) propionic acid | ($C_2$-$C_6$)-alkanediol | Glycerol | Toluene-2,4-diisocyanate |
| 2,2-bis(hydroxymethyl) propionic acid | ($C_2$-$C_6$)-alkanediol | 1,3,5-Trihydroxybenzene | Toluene-2,4-diisocyanate and toluene-2,6-diisocyanate |
| 2,2-bis(hydroxymethyl) propionic acid | ($C_2$-$C_6$)-alkanediol | Glycerol | Toluene-2,4-diisocyanate and toluene-2,6-diisocyanate |
| 2,2-bis(hydroxymethyl) propionic acid | 1,4-Butanediol | 1,3,5-Trihydroxybenzene | Toluene-2,4-diisocyanate |
| 2,2-bis(hydroxymethyl) propionic acid | 1,4-Butanediol | Glycerol | Toluene-2,4-diisocyanate |
| 2,2-bis(hydroxymethyl) propionic acid | 1,4-Butanediol | 1,3,5-Trihydroxybenzene | Toluene-2,4-diisocyanate and toluene-2,6-diisocyanate |
| 2,2-bis(hydroxymethyl) propionic acid | 1,4-Butanediol | Glycerol | Toluene-2,4-diisocyanate and toluene-2,6-diisocyanate |
| 2,2-bis(hydroxymethyl) propionic acid | 1,3-dihydroxyacetone | 1,3,5-Trihydroxybenzene | Toluene-2,4-diisocyanate |
| 2,2-bis(hydroxymethyl) propionic acid | 1,3-dihydroxyacetone | Glycerol | Toluene-2,4-diisocyanate |

TABLE 1-continued

| A1 | A2a | A2b | B |
|---|---|---|---|
| 2,2-bis(hydroxymethyl) propionic acid | 1,3-dihydroxyacetone | 1,3,5-Ttrihydroxybenzene | Toluene-2,4-diisocyanate and toluene-2,6-diisocyanate |
| 2,2-bis(hydroxymethyl) propionic acid | 1,3-dihydroxyacetone | Glycerol | Toluene-2,4-diisocyanate and toluene-2,6-diisocyanate |
| 2,2-bis(hydroxymethyl) propionic acid | Polyethylene glycol with an number average molecular weight Mn of from 200 g/mol to 10,000 g/mol (preferably of from 400 g/mol to 2,500 g/mol) | Glycerol | Isophorone diisocyanate |
| 2,2-bis(hydroxymethyl) propionic acid | 1,3-dihydroxyacetone | Glycerol | Isophorone diisocyanate |

The polymer of the carrier matrix obtained by polyaddition is preferably obtained by emulsion polymerization, particularly preferably by reacting
  i) at least one isocyanate-reactive monomer A, selected from compounds containing at least two functional groups, each carrying at least one Zerewitinoff-reactive hydrogen atom
  ii) at least one polyisocyanate monomer B
by means of emulsion polymerization of an emulsion, containing
  i) in the discontinuous phase magnetic nanoparticles, at least one polar, organic liquid (preferably with a cLogP value <1.5 (25° C.)) and at least an isocyanate-reactive monomer A that differs from the polar, organic liquid, selected from compounds containing at least two functional groups each carrying at least one Zerewitinoff-reactive hydrogen atom, and
  ii) in the continuous phase at least one nonpolar, organic liquid (preferably with a cLogP value >2 (25° C.)),
in the presence of polyisocyanate monomer B, with the proviso that the cLogP value (25° C.) of the polar liquid is smaller than the cLogP value (25° C.) of the nonpolar, organic liquid.

Thereby, in turn, the aforementioned preferred monomers, in particular in the aforementioned preferred combinations, are preferably used.

A substance is a "liquid" or "liquid" if it is present in the liquid physical state at 20° C. and 1013 mbar.

The n-octanol/water partition coefficient P of a substance is often used to define the hydrophilicity or lipophilicity of substances, usually stated as the logarithm on the base of 10, logP. P is the ratio between the concentration of said substance in the n-octanol phase c(octanol) and the concentration of said substance in the water phase c(water)

$$P=c(\text{octanol})/c(\text{water})$$

In the context of the present invention, a calculated LogP value is used, the so-called cLogP value of a substance. To determine the cLogP values used according to the invention, a calculation method was used from the company Advanced Chemistry Development Inc. (ACD) that was described in the article "ACD/LogP method description" in *Perspectives in Drug Discovery and Design*, 19, 2000, pages 99-116. The entire aforementioned article and its disclosure is part of the disclosure of this patent application. The cLogP values (25° C.) were calculated using the software ACD/Percepta 14.0.0 (Build 2726) (Advanced Chemistry Development Inc.) with the ACD/LogP Classic Module.

A particularly preferred particulate solid composite material of this invention is obtained by using the method described in the following. A further object of the invention is therefore a method for producing a particulate solid composite material for nucleic acid purification, containing magnetic nanoparticles embedded in a carrier matrix that is based on at least one polymer obtainable by polyaddition, wherein the method comprises the following steps
  a) Providing a magnetic fluid in form of a suspension containing magnetic nanoparticles and a liquid continuous phase, containing at least one polar organic liquid and less than 5 wt %, preferably less than 2 wt % of water, relative to the weight of the fluid,
  b) Mixing the magnetic fluid with at least one isocyanate-reactive monomer A1, selected from compounds containing
    at least two functional groups each having at least one Zerewitinoff-reactive hydrogen atom, and
    in addition to these at least two functional groups, at least one anionic or potentially anionic residue (preferably selected from the group consisting of carboxylate, sulfonate, or combinations thereof),
  c) Preferably adding at least one surfactant,
  d) Emulsifying the mixture of the previous steps in a liquid continuous phase, containing at least one nonpolar, organic liquid,
  b) Adding at least one polyisocyanate monomer B
  f) Separating the formed composite material after the reaction time is completed and optionally washing,
  with the proviso that the cLogP value (25° C.) of the polar organic liquid is smaller than the cLogP value (25° C.) of the nonpolar organic liquid, and, relative to its weight, the liquid, continuous phase from step d) contains less than 5 wt %, preferably less than 2 wt % of water.

It is essential that in the inventive method the emulsion polymerization proceeds in a milieu that contains little or no water. This can, for example, be achieved when all of the components used are free or almost free from water, i.e., contain less than 5 wt %, in particular less than 2 wt % of water.

In step a) of the method according to the invention, a magnetic fluid is provided that contains a low amount of water and is therefore almost free from water within the meaning of the aforementioned definition.

Unless otherwise specified, data on an amount of water relates to the amount of free water. The amounts of molecularly-bound water or crystal water, which individual components could contain, are not considered. The amount of water can, for example, be determined by means of Karl-Fischer titration according to DIN EN 14346:2007-03 (Method B).

A magnetic fluid according to the invention in which the aforementioned preferable magnetic nanoparticles are suspended in said liquid continuous phase is a suitable magnetic fluid preferred for the method according to the invention.

The magnetic fluid used in step a) has a liquid continuous phase containing at least one polar organic liquid. It is thereby inventively preferred if said polar, organic liquid, has a cLogP value <1.5 (25° C.), particularly preferred a cLogP value <1.0 (25° C.), more particularly preferred a cLogP value <0 (25° C.).

Particularly preferred polar organic liquids used in the method according to the invention are liquid organic compounds having at least one functional group, selected from amide, nitrile, nitro, sulfoxide, N-oxide, lactone, N-alkylpyrrolidone. More particularly preferred suitable polar organic liquids are selected from N-dimethylformamide, acetonitrile, N-methyl-2-pyrrolidone, N-methylformamide, γ-butyrolactone, 4-methyl-1,3-dioxolan-2-one, dimethylsulfoxide, sulfolane, nitromethane, or combinations of at least two of these compounds. Most particularly preferred, at least N, N-dimethylformamide is used as a polar, organic liquid.

The cLogP values (25° C.) of the most particularly preferred polar, organic liquids are summarized in Table 2.

TABLE 2

| cLogP values of preferred polar, organic liquids | |
|---|---|
| Substance | cLogP (25° C.) |
| N,N-dimethylformamide | −1.01 |
| Acetonitrile | −0.45 |
| N-methyl-2-pyrrolidone | −0.40 |
| N-methylformamide | −0.60 |
| γ-butyrolactone | −0.76 |
| 4-methyl-1,3-dioxolan-2-one | −0.41 |
| Dimethylsulfoxide | −1.35 |
| Sulfolane | −0.77 |
| Nitromethane | −0.20 |

The polar, organic liquid is contained in the magnetic fluid in a total amount of from 85 to 99 wt %, in particular of from 92 wt % to 98 wt %, relative to the weight of the magnetic fluid.

It has been found to be inventively advantageous if the polyaddition reaction is allowed to proceed in the presence of at least one suitable catalyst. For this purpose, it is preferred, in particular prior to adding the polyisocyanate monomer B, to mix at least one catalyst for the polyaddition reaction of the monomers A (or A1 and A2) and B into the ferrofluid or the mixture of Step b) or Step c).

Suitable catalysts that can be used according to the invention are e.g., organic compounds of tin, iron, titanium or bismuth such as tin(II) salts of carboxylic acids, e.g., tin(II)acetate, -ethylhexanoate and -diethylhexanoate Dialkyl tin (IV) carboxylates, such as dibutyl and dioctyltin diacetate-maleate, -bis-(2-ethylhexanoate), -dilaurate, tributyltin acetate, bis-(β-methoxycarbonyl-ethyl) tin dilaurate and bis-(β-acetyl-ethyl) tin dilaurate are equally suitable. Also suitable are tin oxides and tin sulfides as well as tin thiolates.

Further suitable catalysts within the meaning of the invention are derivatives of morpholine. Specific examples of such morpholino compounds are bis(2-(2,6-dimethyl-4-morpholino)ethyl)-(2-(4-morpholino)ethyl)amine, bis(2-(2,6-dimethyl-4-morpholino) ethyl)-(2-(2,6-diethyl-4-morpholino)ethyl)amine, tris(2-(4-morpholino)ethyl)amine, tris(2-(4-morpholino)propyl)amine, tris(2-(4-morpholino) butyl)amine, tris(2-(2,6-diethyl-4-morpholino)ethyl)amine, tris(2-(2,6-diethyl-4-morpholino)ethyl)amine, tris(2-(2-methyl-4-morpholino)ethyl)amine or tris(2-(2-ethyl-4-morpholino)ethyl)amine, dimethylaminopropylmorpholine, bis-(morpholinopropyl)methylamine, diethylaminopropylmorpholine, bis-(morpholino-propyl)-ethylamine, bis(morpholinopropyl)propylamine, morpholinopropylpyrrolidone or N-morpholinopropyl-N'-methylpiperazine, dimorpholinodiethylether (DMDEE) or di-2, 6-dimethylmorpholinoethylether.

More preferred in the context of the present invention at least one aliphatic tertiary amine, in particular with a cyclic structure, and/or at least one unsaturated bicyclic amine is used. In particular, as a preferred catalyst of the inventive method at least one compound is used from the group consisting of diaza-bicyclo-octane (DABCO), triethylamine, dimethylbenzylamine, bis-dimethylaminoethylether (Calalyst A 1, UCC), tetramethylguanidine, bis-dimethylaminomethylphenol, 2-(2-dimethylaminoethoxy)ethanol, 2-dimethylaminoethyl-3-diemthylaminopropylether, bis(2-dimethylaminoethyl)ether, N,N-dimethylpiperazine, N-(2-hydroxyethoxyethyl)-2-azanorbomane, diazabicycloundecene (DBU), N,N,N,N-tetramethylbutane-1,3-diamine, N,N, N,N-tetramethylpropane-1,3-diamine, N,N,N,N-tetramethylhexane-1,6-diamine or combinations thereof. The tertiary amine can also be present in a oligomerized or polymerized form, e.g., as N-methylated polyethyleneimine.

The catalysts are preferably added in an amount of from 0.0001 to 5 wt %, preferably of from 0.001 to 2 wt %, relative to the weight of the compounds used that are reactive with isocyanates (i.e., monomer A1, A2, A2a, A2b).

Surfactants can form aggregates, so-called micelles, in water. Such aggregates are referred to as micelles that form from surfactant molecules in aqueous solutions above a certain temperature (Krafft point) and characteristic concentration. In accordance with the general understanding in the prior art, this characteristic concentration, also referred to as "critical micelle concentration" (CMC), is the concentration of the corresponding substance at which said substance begins to form micelles, and every additional molecule that is added to the system transfers into the micelle. According to the invention, compounds are counted as surfactants when they are able to form micelles in water at 20° C. at a defined CMC.

According to the invention, the surfactants are used independently of the addition of the previously defined isocyanate-reactive monomers; therefore, according to the definition, surfactants within the meaning of the invention must not be counted as parts of isocyanate-reactive compounds, in particular not the monomers A1, A2, A2a and A2b.

Nonionic surfactants are preferably added in step c) of the method according to the invention.

It was shown that especially those nonionic surfactants are particularly suitable that have an HLB value (according to Griffin) of from 1 to 20, in particular of from 1 to 10.

More particularly preferred, nonionic surfactants that carry at least one hydroxyl group are added in Step c) of the method according to the invention.

Most particularly preferred, at least one sorbic acid ester of the following formula (II) is added as non-ionic surfactant in Step c) of the method according to the invention.

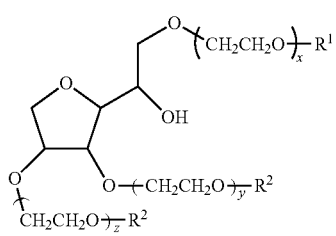

(II)

where the sum of x+y+z represents the number 0 to 100, in particular 0 to 80, most particularly preferred zero, $R^1$, $R^2$ and $R^3$ independently of one another represent a hydrogen atom, a saturated ($C_6$ to $C_{20}$) acyl group or an unsaturated ($C_6$ to $C_{20}$) acyl group with the provisio that at least one of the $R^1$, $R^2$ or $R^3$ residues represents a saturated ($C_6$ to $C_{20}$) acyl group or an unsaturated ($C_6$ to $C_{20}$) acyl group.

Particularly preferably, according to formula (II) y and z represent zero, x represents an integer between 0 to 20 (in particular x=0), $R^1$ represents a saturated ($C_6$ to $C_{20}$) acyl group or an unsaturated ($C_6$ to $C_{20}$) acyl group and $R^2$ and $R^3$ represent a hydrogen atom.

Sorbic acid esters of formula (II) are preferred that have an HLB value (according to Griffin) of from 1 to 20, in particular of from 1 to 10.

Particularly preferred nonionic surfactants are selected from (optionally ethoxylated) sorbitan monolaurate, sorbitan monooleate, sorbitan monostearate, sorbitan trioleate.

Corresponding nonionic surfactants are available, for example, under the designations Span 60, Span 65, Span 80, Span 85 or Brij 25.

The surfactant, in particular the nonionic surfactant (preferably the surfactant of formula (II)) is preferably added in a total amount of from 0 wt % to 60 wt %, particularly preferred of from 0 wt % to 30 wt %, relative to the weight of the magnetic fluid.

Most particularly preferred, the monomers preferably used for preparing the aforedescribed composite materials according to the invention are reacted in the presence of a surfactant that is added in Step c). According to the invention, the use of at least one nonionic surfactant, in particular of sorbic acid esters of formula (II), is, in turn, preferred in combination with the monomers listed as preferable (in particular in Table 1).

Prior to the emulsification, a nonpolar organic liquid is added to the mixture from Step b) or Step c) of the production method according to the invention. It was shown to be particularly effective if the nonpolar organic liquid from Step d) has a cLogP value >2.0 (25° C.). In turn, it is most particularly preferred if said polar, organic liquid has a cLogP value <1.5 (25° C.) (in particular a cLogP value <1.0 (25° C.), particularly preferred a cLogP value <0 (25° C.)) and said nonpolar, organic liquid has a cLogP value >2.0 (25° C.).

TABLE 3 cLogP values of preferred nonpolar, organic liquids

| Substance | cLogP (25° C.) |
| --- | --- |
| Cyclohexane | 3.39 |
| Hexane | 3.94 |
| Pentane | 3.41 |
| Heptane | 4.47 |
| Octane | 5.01 |

According to the invention, it is preferred that the nonpolar organic liquid is selected from aliphatic hydrocarbons, alicyclic hydrocarbons, triglycerides (in particular vegetable oil such as, for example, rapeseed oil), silicone oil, vegetable oil, or combinations of at least two of these compounds. Particularly preferably, the nonpolar organic liquid is selected from liquid hydrocarbon (in particular paraffin oil, petroleum ether, liquid hydrocarbons having 5 to 16 carbon atoms), silicone oil, vegetable oil, or combinations thereof.

The polar organic liquid is preferably used at a volume ratio relative to the volume of the nonpolar organic liquid of from 1:1 to 1:20, preferably of from 1:2 to 1:15, particularly preferably of from 1:5 to 1:10.

Although the use of a surfactant according to Step c) is preferred, the emulsification Step d) can also be performed in the absence of a surfactant under sufficient mechanical mixing (e.g., sufficient stirring speed).

According to Step d) of the method according to the invention, the mixture is preferably emulsified under stirring. For example, known KPG stirrers with known stirrers systems can be used for this purpose (e.g. mixers RW 28 digital or RW 47 digital from IKA-Werke GmbH & Co. K G, Staufen). All conventional designs can be used as stirring systems (propeller stirrer, turbine stirrer, disc stirrer, surface stirrer, anchor stirrer, spiral stirrer).

The preferred stirring speed is derived as a function of the stirring system used, the diameter, and the design of the stirrer (e.g., propellers stirrer, three blade or four blade) and the geometry of the reaction vessel. In the embodiment described in the exemplary reactions (1 L reaction vessel, KPG-stirrer model RZR 2102 control from Heidolph, three blade propeller stirrer with a shaft diameter of 10 mm, a shaft length of 600 mm, a stirrer diameter of 75 mm) it is preferred to stir at a stirring speed in the range between 150 rpm and 1200 rpm, particularly preferred between 200 rpm and 600 rpm.

The emulsification Step d) is preferably performed at a temperature of from 35° C. to 90° C., in particular of from 40° C. to 80° C., more particularly preferred of from 45° C. to 75° C. It is most particularly preferred when the preferred stirring parameters and the preferred temperatures are preset.

In the context of this production method, the aforementioned preferred monomers A1, A2, A2a, A2b, B are in turn preferably used, in particular in the aforementioned preferred combinations.

The polyisocyanate monomers preferably used in Step e) of the production method further have a cLogP value (25° C.) of >1.5, in particular of >2.0, particularly preferred of >2.5.

TABLE 4 cLogP values (25° C.) of preferred polyisocyanate monomers

| Substance | cLogP (25° C.) |
|---|---|
| Toluene-2,4-diisocyanate (m-TDI) | 3.47 |
| Toluene-2,6-diisocyanate | 3.47 |
| Isophorone diisocyanate | 4.67 |
| Hexamethylene diisocyanate | 3.03 |
| Methylene diphenyl diisocyanate | 4.93 |

By using a specific ratio between the functional groups with Zerewitinoff-reactive hydrogen atoms of all isocyanate-reactive monomers used for synthesis and the isocyanate groups of all polyisocyanate monomers used for synthesis, the properties of the composite material can be optimized in terms of magnetic separation and the performance of the production method. Therefore, a method according to the invention is preferred wherein the substance ratio between the amount of substance n(Zerewitinoff) of the functional groups with Zerewitinoff-active hydrogen atoms of all isocyanate reactive monomers used and the amount of substance n(NCO) of the isocyanate groups of all polyisocyanate monomers used is between 5:1 and 1:5, particularly preferred between 4:1 and 1:4, more particularly preferred between 2:1 and 1:3, most particularly preferred between 1.5:1 and 1:2.

According to the invention, it is preferred that before the polyisocyanate monomer B is added, it is admixed with at least one nonpolar organic liquid defined in Step d).

The addition of the polyisocyanate monomer B is preferably performed under stirring. The stirring speeds and temperatures specified for Step d) are preferable.

The polyaddition reaction is also preferably performed under stirring, particularly preferable using the stirring parameters described for Step d).

It is furthermore preferred that the polyaddition reaction is performed at a temperature of from 35° C. to 90° C., in particular of from 40° C. to 80° C., most particularly preferred of from 45° C. to 75° C.

The reaction time of the polyaddition reaction, calculated from the time the polyisocyanate monomer B is added, ranges between 10 and 150 hours, preferably between 24 and 120 hours, particularly preferably between 36 and 100 hours. It is thereby particularly preferred if at least one catalyst is used for the polyaddition and the reaction mixture is stirred and heated. The aforementioned catalysts, stirring parameters, and temperatures are thereby preferably pre-set during the reaction period.

The reaction can be stopped, for example, by addition of water after the reaction time has expired.

For purification, the magnetic composite particles obtained are suspended e.g., in water or various organic solvents, such as e.g., ethanol or acetone, which serve as wash solutions, and collected (preferably by applying a magnetic field) and removed again from said wash solution.

The aforedescribed particulate solid composite material according to the invention is preferably used for purification of nucleic acids.

A further object of the invention is therefore a method for purifying nucleic acids from a nucleic acid-containing, biological sample, comprising the following steps:

a) Providing an aqueous sample, containing nucleic acids in solubilized form;

b) Depositing at least nucleic acids from the aqueous sample onto a particulate solid composite material according to the invention (see above).

c) Separating the particulate solid composite material loaded with nucleic acids from Step b) by applying a magnetic field and optionally washing the separated particles with a wash solution;

d) Bringing into solution the remaining nucleic acid from the particulate solid composite material treated according to Step c) using a resuspension buffer and separating the particulate solid composite material from the nucleic acid-containing solution.

The purification method according to the invention is a simple "bind-wash-elute" method. In the context of a "bind-wash-elute" method, in the inventive method nucleic acids are separated from the aqueous sample together with unwanted substances using known methods, and a large portion of contaminants are removed from the separated components of the sample by using at least one wash solution. With this method, the contamination can be significantly reduced in a rapid and cost-efficient manner and the eluted nucleic acids, in particular the eluted DNA, can be used directly for subsequent applications, for example, a polymerase chain reaction (PCR), depending on the method selected for the nucleic acid isolation.

Nucleic acids include RNA and DNA of various chain lengths, in particular having more than fifteen nucleotides, such as for example single- and double-stranded bacterial, viral, human, animal, or plant RNA or DNA, in particular genomic DNA, mitochondrial DNA, plasmids, mRNA, tRNA, rRNA, miRNA and other short RNA species, in particular having a chain length of from 15 to 25 nucleotides. "Nucleic acid" according to the invention is preferably understood as meaning deoxyribonucleic acid (DNA).

A biological sample is used to prepare the aqueous nucleic acid-containing sample. Any biological material that contains at least nucleic acids is suitable as said biological sample, such as bacterial cultures, animal or human tissue, tissue components, body fluids such as saliva, sputum, cerebral spinal fluid, whole blood, serum, or plasma. Bacteria, yeast, and other fungi or viruses are likewise understood as meaning "sample material," as well as PCR amplification reactions containing primers and DNA fragments, or cell culture supernatants. Sample material may comprise environmental or food samples. Artificial sample material, e.g., containing synthetic or in vitro-generated nucleic acids, also falls within the scope of the present invention.

To provide an aqueous sample containing nucleic acids in solubilized form, the biological sample can first be disrupted, i.e., lysed, during Step a) of the purification method according to the invention in order to release the nucleic acids from the material. Lysis can comprise mechanical, chemical and/or enzymatic lysis. Lysis of the biological sample is often supported by a suitable buffer chemistry that, for example, contains detergents. The skilled person is familiar with suitable lysis conditions.

In Step b) of the purification method according to the invention, the nucleic acid is separated from the aqueous sample, usually together with contaminations, by means of any method known to the skilled person. The method according to the invention is not limited to a certain separation principle. Various methods that can be used are found in the prior art and are known to the skilled person. Said methods comprise, for example, the use of chaotropic salts, the use of anti-chaotropic salts, precipitation (e.g. precipitation using polyethylene glycol or lower alcohols), filtration, exploitation of hydrophobic interactions for nucleic acid binding to a carrier material, and other methods.

A preferred form of isolation is characterized in that in Step b) at least nucleic acids are deposited via binding, in particular via adsorption or precipitation, onto the surface of the particulate solid composite material according to the invention. It is thereby particularly preferred if binding buffer is added to the sample in Step b) in order to deposit onto the solid composite material according to the invention.

The binding buffer preferably contains at least one chaotropic salt and/or at least one monoalcohol with up to 16 carbon atoms.

According to prevailing theories, the chaotropic salts destroy the ordered water structure around compounds that are solubilized in water. Chaotropic salts are therefore defined such that they denature proteins, increase the solubility of nonpolar substances in water, and disrupt hydrophobic interactions. It is known that in the presence of chaotropic salts nucleic acids reversibly bind to carrier materials, in particular to silicates and to other inorganic carrier materials. The chaotropic salts thereby destroy the hydrate shell around the nucleic acids and create a hydrophobic microenvironment. Under these conditions, nucleic acids and also some contaminants bind to the solid carrier material, while proteins and other contaminants do not bind and are washed off. The strength of the chaotropic character of a salt is described by the so-called Hofmeister series.

The chaotropic salt or chaotropic salts is/are preferably contained in the binding buffer at a concentration of from 1 to 6 mol/L.

In the context of the present invention, chaotropic salts that are preferably used are sodium perchlorate, sodium iodide, guanidinium isothiocyanate, guanidinium hydrochloride, potassium thiocyanate, guanidinium nitrate, guanidinium carbonate, urea, or combinations thereof.

It is particularly preferred according to the invention when the binding buffer contains at least one chaotropic salt or at least one monoalcohol with up to 16 carbon atoms or an organic polymer.

The deposition of the nucleic acid onto the composite material according to the invention can be achieved by bringing the sample into contact with the composite material according to the invention. The particles of the inventive composite material can also be directly added to the sample. In order to improve the binding conditions, binding buffer can be added to the sample after the particles have been added (see above).

As a further preferred option for deposition according to Step b), at least the nucleic acid from the aqueous sample can be deposited as a solid onto the inventive composite material via precipitation. For this purpose, a precipitation reagent can be added to the aqueous sample that precipitates the nucleic acid as a solid out of the aqueous sample. The precipitation reagent preferably contains one compound selected from tripropylene glycol (preferably in combination with a ($C_1$-$C_4$) alcohol (particularly preferred methanol, ethanol, n-propanol or isopropanol, more particularly preferred ethanol)), polyethylene glycols having a molecular weight of between 300 and 10,000 g/mol, polypropylene glycols having a molecular weight of between 300 and 10,000 g/mol, cationic detergents (such as hexadecyltrimethylammonium bromide (CTAB), pyridinium salts, or quaternary ammonium compounds having a long-chained hydrocarbon residue ($C_6$-$C_{18}$) and three residues, selected from short hydrocarbon residues ($C_1$-$C_3$) or hydrogen), ethanol, n-propanol, isopropanol, or combinations thereof.

In Step c) of the inventive purification method, the nucleic-acid containing, particulate solid composite material is separated by applying a magnetic field and optionally further purified by washing the isolated particles with a wash solution.

The wash solution optionally used in Step c) preferably contains an organic amine compound (see above). While maintaining the aforementioned mandatory properties, the organic amine compound is, for example, selected from at least one compound of the group that is formed from compounds having an amino group, compounds having at least two amino groups, compounds having at least one amino group and at least one hydroxyl group, compounds having at least two amino groups and at least one hydroxyl group (particularly preferred selected from at least one compound of the group that is formed from compounds having an amino group, compounds having at least one amino group and at least one hydroxyl group).

It is inventively preferred if said amine compound has a molar mass of from 80 to 500 g/mol.

To improve the solubility in water, it is preferred if the amine compound has at least two hydroxyl groups.

Especially suitable organic amine compounds preferably contain optionally substituted hydrocarbon residues with 1 to 6 carbon atoms. Hydroxy or alkoxy are particularly suitable as substituents.

The organic amine compound of the wash solution is, for example, selected from triethylamine, triethanolamine, 2-amino-2-(hydroxymethyl)propane-1,3-diol (TRIS), 2,2-bis(hydroxymethyl)-2,2'2"-nitrilotriethanol (BIS-TRIS) 1,3-bis[tris(hydroxymethyl) methyl-amino]propane (BIS-TRIS propane), diisopropylamine, triisopropylamine, or combinations thereof. More particularly preferred, the organic amine compound of the wash solution is selected from triethylamine, triethanolamine, 2-amino-2-(hydroxymethyl)-propane-1,3-diol (TRIS), 2,2-bis(hydroxymethyl)-2,2',2"-nitrilotriethanol (BIS-TRIS) 1,3-bis[tris (hydroxymethy)methyl-amino]propane (BIS-TRIS propane), or combinations thereof.

The wash solution according to Step c) must contain at least one organic solvent that differs from said amine compounds. The organic solvent is preferably contained in the wash solution in a total amount of from 20 to 80 wt %, relative to the total weight of the wash solution.

It has proved to be advantageous if the wash solution contains at least one monoalcohol as preferred organic solvent. Particularly preferably, the wash solution contains at least one $C_1$-$C_6$ monoalcohol as the organic solvent, in particular ethanol, isopropanol, or combinations thereof. It is thereby most particularly preferred if the wash solution contains the $C_1$-$C_6$ monoalcohol in a total amount of from 20 wt % to 80 wt %, relative to the total weight of the wash solution.

In Step d) of the inventive purification method, the nucleic acid remaining in the components that were washed and deposited according to Step c) are brought into solution by means of a resuspension buffer and the particulate solid composite material is separated from the nucleic acid-containing solution.

During resuspension, the remaining, separated nucleic acid is solubilized in the resuspension buffer and separated from the magnetic composite material. Preferred resuspension buffers suitable for bringing the remaining, deposited nucleic acid into solution have a low ionic strength. A suitable resuspension buffer is, for example, a buffer containing of from 5 to 10 mM TRIS (optionally in combination with up to 1 mM ethylenediaminetetraacetic acid (EDTA)).

The resuspension according to Step d) of the inventive method is preferably performed by rinsing the particulate solid composite material with the resuspension buffer, followed by magnetically separating the inventive composite particles. The rinsing is preferably accomplished by a flow of the resuspension buffer through the solid composite material. The direction of flow is preferably determined by stirring, applying a vacuum, or by centrifugation. When automated platforms are used, the rinsing can also be performed by repeatedly pipetting the added resuspension buffer up and down or by repeatedly moving the tip combs up and down.

A further object of the invention is a kit for purifying nucleic acids, comprising a particulate solid composite material according to the invention (see above) and at least one additional component, selected from a user manual for performing the aforedescribed purification method according to the invention, binding buffer, wash buffer, resuspension buffer to bring the purified nucleic acids into solution.

All preferred embodiments of the purification method according to the invention also apply to the purification method described in the user manual of the kit.

All preferred embodiments of the composite material according to the invention also apply to the kit.

Particularly preferred embodiments of the invention are summarized in the following points 1 to 28:

1. Method for producing a particulate solid composite material for nucleic acid purification, containing magnetic nanoparticles embedded in a carrier matrix based on at least one polymer obtainable by polyaddition, characterized in that the method comprises the following steps
   a) Providing a magnetic fluid in form of a suspension, containing magnetic nanoparticles and a liquid continuous phase containing at least one polar organic liquid and less than 5 wt %, preferably less than 2 wt % of water, relative to the weight of the fluid,
   a) Mixing the magnetic fluid with at least one isocyanate-reactive monomer A1, selected from compounds containing
      at least two functional groups each having at least one Zerewitinoff-reactive hydrogen atom, and
      in addition to these at least two functional groups, at least one anionic or potentially anionic residue (preferably selected from the group consisting of carboxylate, sulfonate, or combinations thereof),
   c) Preferably adding at least one surfactant,
   d) Emulsifying the mixture obtained in the previous steps in a liquid continuous phase, containing at least one nonpolar, organic liquid,
   b) Adding at least one polyisocyanate monomer B,
   f) Separating the formed composite material after the reaction time is completed and optionally washing,
   with the provisio that the cLogP value (25° C.) of the polar organic liquid is smaller than the cLogP value (25° C.) of the nonpolar organic liquid, and the liquid, continuous phase from Step d) contains less than 5 wt %, preferably less than 2 wt % of water, relative to the weight of the continuous phase.
2. Method according to Point 1, wherein said polar, organic liquid has a cLogP value <1.5 (25° C.) and said nonpolar, organic liquid has a cLogP value >2.0 (25° C.).
3. Method according to one of the preceding Points, wherein the magnetic nanoparticles are selected from ferromagnetic nanoparticles, ferrimagnetic nanoparticles, or mixtures thereof, preferably from superparamagnetic nanoparticles.
4. Method according to one of the preceding Points, wherein the magnetic nanoparticles comprise iron oxide, in particular magnetite, maghemite, or mixtures thereof.
5. Method according to one of the preceding Points, wherein the average particle size of the magnetic nanoparticles is at most 200 nm, preferably at most 100 nm, particularly preferably at most 50 nm.
6. Method according to one of the preceding Points, wherein the average particle size of the magnetic nanoparticles is at least 1 nm, in particular at least 5 nm.
7. Method according to one of the preceding Points, wherein the polar organic liquid has a cLogP value <1.0 (25° C.).
8. Method according to one of the preceding Points, wherein the isocyanate-reactive monomer A is selected from 2,2-bis(hydroxymethyl)propionic acid, 2,3-diaminobenzoic acid, 2,4-diaminobenzoic acid, 2,5-diaminobenzoic acid, 2,6-diaminobenzoic acid, 3,4-diaminobenzoic acid, 3,5-diaminobenzoic acid, 2,2-bis(hydroxymethyl)acetic acid, 2,2,2-tri(hydroxymethyl)acetic acid, 2,2-bis(hydroxymethyl)propionic acid, 2,2-bis(hydroxymethyl)butyric acid, 2,2-bis(hydroxymethyl)pentanoic acid, 2,5-dihydroxy-3-methylpentanoic acid, 3,5-dihydroxy-3-methylpentanoic acid, 4,5-dihydroxy-3-methylpentanoic acid, 3,4-dihydroxy-3-methylpentanoic acid, 2,3-dihydroxy-3-methylpentanoic acid, 2,4-dihydroxy-3-methylpentanoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 2,3-dihydroxysuccinic acid, 2,5-diaminopentanoic acid, 3,5-diaminopentanoic acid, 4,5-diaminopentanoic acid, 2,3-dihydroxybenzenesulfonic acid, 3,4-dihydroxybenzenesulfonic acid, 2,4-dihydroxybenzenelsulfonic acid, 2,5-dihydroxybenzene sulfonic acid, 3,5-dihydroxybenzenesulfonic acid, 2,3-diaminobenzenesulfonic acid, 3,4-diaminobenzenesulfonic acid, 2,4-diaminobenzenesulfonic acid, 2,5-diaminobenzenesulfonic acid, 3,5-diaminobenzenesulfonic acid, 3,4-dihydroxy-2-toluenesulfonic acid, 3,4-diamino-2-toluenesulfonic acid, 4,5-dihydroxy-2-toluenesulfonic acid, 4,5-diamino-2-toluenesulfonic acid, 5,6-dihydroxy-2-toluenesulfonic acid, 5,6-diamino-2-toluenesulfonic acid, 3,5-dihydroxy-2-toluenesulfonic acid, 3,5-diamino-2-toluenesulfonic acid, 3,6-dihydroxy-2-toluenesulfonic acid, 3,6-diamino-2-toluenesulfonic acid, 4,6-dihydroxy-2-toluenesulfonic acid, 4,6-diamino-2-toluenesulfonic acid, 2,4-dihydroxy-3-toluenesulfonic acid, 2,4-diamino-3-toluenesulfonic acid, 2,5-dihydroxy-3-toluenesulfonic acid, 2,5-diamino-3-toluenesulfonic acid, 2,6-dihydroxy-3-toluenesulfonic acid, 2,6-diamino-3-toluenesulfonic acid, 4,5-dihydroxy-3-toluenesulfonic acid, 4,5-diamino-3-toluenesulfonic acid, 4,6-dihydroxy-3-toluenesulfonic acid, 4,6-diamino-3-toluenesulfonic acid, 5,6-dihydroxy-3-toluenesulfonic acid, 5,6-diamino-3-toluenesulfonic acid, 2,3-dihydroxy-4-toluenesulfonic acid, 2,3-diamino-4-toluenesulfonic acid, 2,5-dihydroxy-4-toluenesulfonic acid, 2,5-diamino-4-toluenesulfonic acid, 2,6-dihydroxy-4-toluenesulfonic acid, 2,6-diamino-4-toluenesulfonic acid, 3,5-dihydroxy-4-toluenesulfonic acid, 3,5-diamino-4-toluenesulfonic acid, 3,6-dihydroxy-4-toluenesulfonic acid, 3,6-diamino-4-toluenesulfonic acid, 5,6-dihydroxy-4-toluenesulfonic acid, 5,6-diamino-4-toluenesulfonic acid, or combinations thereof.
9. Method according to one of the preceding Points, wherein, in addition to at least one monomer A1, at least one additional monomer A2 is used as isocyanate-reactive monomer, selected from non-ionic compounds containing at least two functional groups each carrying at least one Zerewitinoff-reactive hydrogen atom.

10. Method according to one of the preceding Points, wherein said functional groups of the isocyanate-reactive monomer are independently of one another selected from the group consisting of hydroxyl, amino, thiol, ketimine, ketazine, oxazolidine, or combinations thereof.

11. Method according to one of the preceding Points, wherein the isocyanate-reactive monomer A2 is selected from organic polyols, polyether polyols, polyester polyols, polycarbonate polyols, polyetherestercarbonate polyols, amino alcohols, organic polyamines, organic polyalkyleneamines, or combinations thereof, preferably selected from organic diols, organic diamines, organic polyalkylene glycols, organic polyether diols, organic polyesterdiols, polycarbonate diols, polyetherestercarbonate diols, or combinations thereof.

12. Method according to Point 11, wherein the isocyanate-reactive monomer A2 has a number average molecular weight Mn of from 200 g/mol to 10,000 g/mol (preferably of from 400 g/mol to 2,500 g/mol) and is preferably selected from organic polyalkylene glycols, organic polyether diols, organic polyester diols, or combinations thereof.

13. Method according to Point 11 or 12, wherein the isocyanate-reactive monomer A2 comprises a first isocyanate-reactive monomer A2a having two Zerewitinoff-reactive hydrogen atoms and a second isocyanate-reactive monomer A2b having three Zerewitinoff-reactive hydrogen atoms, whereby the first isocyanate-reactive monomer A2a is selected from compounds having two hydroxyl groups, amino groups, thiol groups, ketimine groups, ketazine groups, oxazolidine groups, or combinations thereof, and the second isocyanate-reactive monomer A2b is selected from compounds having three hydroxyl groups, amino groups, thiol groups, ketimine groups, ketazine groups, oxazolidine groups, or combinations thereof.

14. Method according to one of the preceding Points, wherein at least one non-ionic surfactant, preferably containing at least one hydroxyl group, is added as the surfactant in Step c).

15. Method according to one of the preceding Points, wherein the nonpolar organic liquid has a cLogP value >2.5 (25° C.).

16. Method according to one of the preceding Points, wherein the nonpolar organic liquid is selected from at least one liquid hydrocarbon (in particular paraffin oil, petroleum ether, liquid hydrocarbons having 5 to 16 carbon atoms), silicone oil, vegetable oil, or mixtures thereof.

17. Method according to one of the preceding Points, wherein the at least one polyisocyanate monomer B is selected from organic diisocyanates of the following formula (I), $$O=C=N-R-N=C=O \qquad (I)$$

wherein R represents a cycloaliphatic ($C_{3-15}$) hydrocarbon residue, aromatic ($C_{6-15}$) hydrocarbon residue, araliphatic ($C_{6-18}$) hydrocarbon residue or aliphatic ($C_{3-15}$) hydrocarbon residue.

18. Method according to one of the preceding Points, wherein the substance ratio between the amount of substance n(Zerewitinoff) of the functional groups having Zerewitinoff-active hydrogen atoms of all isocyanate reactive monomers used and the amount of substance n(NCO) of the isocyanate groups of all polyisocyanate monomers used is from 5:1 to 1:5, particularly preferred from 4:1 to 1:4, more particularly preferred from 2:1 to 1:3, most particularly preferred from 1.5:1 to 1:2.

19. Particulate solid composite material for nucleic acid purification, containing magnetic nanoparticles embedded in a carrier matrix based on at least one polymer obtained by polyaddition of
    a) at least one isocyanate-reactive monomer A, selected from compounds containing
        at least two functional groups each having at least one Zerewitinoff-reactive hydrogen atom, and,
        in addition to these at least two functional groups, carrying at least one anionic or potentially anionic residue (preferably selected from the group consisting of carboxylate, sulfonate or combinations thereof),
    with
    b) at least one polyisocyanate monomer B,
    with the provisio that said polyaddition occurs in the presence of magnetic nanoparticles.

21. Particular solid carrier matrix according to Point 19 or 20, wherein the particulate solid composite material exhibits said carrier matrix as particle core in which at least magnetic nanoparticles are embedded, whereby the material constituting the carrier matrix contains more than 50 wt %, in particular more than 60 wt %, particularly preferred more than 70 wt %, more preferred more than 80 wt %, most preferred more than 90 wt % of said polymer.

22. Particulate solid composite material according to one of Points 19 to 21, wherein the magnetic nanoparticles are contained in said composite material in an amount of at least 40 wt %, particularly preferred in an amount of at least 50 wt %, more particularly preferred in an amount of at least 60 wt %, most preferred in an amount of at least 75 wt %, relative to the total weight of the inventive composite material.

23. Particulate solid composite material according to one of Points 19 to 22, wherein the particles of the inventive particulate solid composite material have an average particle size (average volume) of from 0.5 μm to 50 μm, in particular of from 0.6 to 30 μm, most particularly preferably of from 0.6 μm to 10 μm.

24. Particulate solid composite material according to one of Points 19 to 23, wherein the polymer of the carrier matrix is obtained by reaction of
    i) at least one isocyanate-reactive monomer A, selected from compounds containing at least two functional groups, each carrying at least one Zerewitinoff-reactive hydrogen atom
    ii) at least one polyisocyanate monomer B
    by means of emulsion polymerization of an emulsion, containing
    i) in the discontinuous phase magnetic nanoparticles, at least one polar, organic liquid (preferably with a cLogP value <1.5 (25° C.)) and at least an isocyanate-reactive monomer A that differs from the polar, organic liquid, selected from compounds containing at least two functional groups each carrying at least one Zerewitinoff-reactive hydrogen atom, and
    ii) in the continuous phase at least one nonpolar, organic liquid (preferably having a cLogP value >2 (25° C.)),
    in the presence of polyisocyanate monomer B, with the provisio that the cLogP value (25° C.) of the polar organic fluid is smaller than the LogP value (25° C.) of the nonpolar, organic fluid.

25. Particulate solid composite material, in particular according to one of the Points 19 to 24, wherein said material is obtained using a method according to one of the Points 1 to 18.
26. Use of a particulate solid composite material according to one of the Points 19 to 25 for purification of nucleic acids.
27. Method for purification of nucleic acids from a nucleic acid-containing, biological sample, comprising the following steps:
   a) Providing an aqueous sample, containing nucleic acids in solubilized form;
   b) Depositing at least nucleic acids from the aqueous sample onto a particulate solid composite material according to one of the Points 19 to 25;
   c) Separating the nucleic acid-containing particulate solid composite material by applying a magnetic field and optionally washing the separated particles with a wash solution;
   d) Bringing into solution the remaining nucleic acid from the particulate solid composite material treated according to Step c) using a resuspension buffer and separating the particulate solid composite material from the nucleic acid-containing solution.
28. Kit for purifying nucleic acids comprising a particulate solid composite material according to one of Points 19 to 25 and at least one additional component, selected from a user manual for performing a method according to Point 27, binding buffer, wash buffer, resuspension buffer for bringing the purified nucleic acids into solution.

EXAMPLES

I. Preparation of the Magnetic Fluid

Example 1: Preparation Ferrofluid F1

44.86 g iron(III)-chloride hexahydrate and 16.50 g iron (II) chloride tetrahydrate were added to a 3 L beaker and dissolved in 1900 mL DI water under stirring at 660 rpm (KPG stirrer (Heidolph, model RZR 2102 control) with a three blade propeller stirrer (VWR, item no.: BOHLC378-20, shaft diameter 10 mm, shaft length 600 mm, stirrer diameter 75 mm)). 100 mL of a 25% ammonium hydroxide solution was added dropwise using a dropping funnel. After a 30-minute reaction time, the precipitate formed was separated from the supernatant using an NdFeB magnet and washed three times with DI water. The particles were dispersed in 600 mL DI water using an ultrasonic probe (Branson, DIGITAL Sonifier®, model 450, probe 18 mm) with an amplitude of 70% and an ultrasound time of 30 minutes (pulse rate: 1 s on, 0.5 s off). 3.5 g of sodium nitrate dihydrate was added to the dispersion and dispersing repeated using the ultrasonic probe (amplitude of 70% pulse rate: 1 s on, 0.5 s off).

400 mL of water was distilled off from the ferrofluid at 70° C. and as many particles as possible were subsequently separated from the still warm ferrofluid using an NdFeB magnet. At the end of the separation process, 200 mL of N,N-dimethylformamide heated to 80° C. was added in order to improve the separation process. The separated particles were washed four times with 400 mL N,N-dimethylformamide (also heated to 80° C.). The washed particles were dispersed in 300 mL of N,N-dimethylformamide using the ultrasonic probe (amplitude 70%, 30 minutes, pulse rate: 1 s on, 0.5 s off). The ferrofluid obtained in this manner was centrifuged for 10 minutes at 3,000 rpm (Hettich centrifuges, ROTIXA 50 RS) and separated from the pellet.

Immediately before using the solid composite materials for synthesis, the ferrofluid was dispersed again with the ultrasonic probe (amplitude 70%, 15 minutes, pulse rate: 1 s on, 0.5 s off).

Water Content

To determine the water content of the ferrofluid, 100 mL of the ferrofluid was distilled to complete dryness and the solvent collected in a flask cooled with liquid nitrogen. The water content was determined by means of Karl-Fischer titration according to DIN EN 14346:2007-03 (method B).

Water content: 0.2 wt %

Solid Residue

To determine the solid residue, 47.996 g of the freshly dispersed ferrofluid was evaporated in a beaker to complete dryness at 150° C. and subsequently dried in the drying cabinet for 30 minutes at 160° C. After drying 2.665 g of solid remains.

Example 2: Preparation Ferrofluid F2

44.86 g iron(III)-chloride hexahydrate and 16.50 g iron (II) chloride tetrahydrate were added to a 3 L beaker and dissolved in 1900 mL DI water under stirring at 660 rpm (KPG stirrer (Heidolph, model RZR 2102 control) with a three blade propeller stirrer (VWR, item no.: BOHLC378-20, shaft diameter 10 mm, shaft length 600 mm, stirrer diameter 75 mm)). 100 mL of a 25% ammonium hydroxide solution was added dropwise using a dropping funnel. After a 30-minute reaction time, the precipitate formed was separated from the supernatant using an NdFeB magnet and washed three times with DI water. The particles were dispersed in 600 mL DI water using an ultrasonic probe (Branson, DIGITAL Sonifier®, model 450, probe 18 mm) with an amplitude of 70% and an ultrasound time of 30 minutes (pulse rate: 1 s on, 0.5 s off). The particles were separated from the solution, which was still warm after the ultrasound treatment (70° C.), and washed four times with 400 mL of N,N-dimethylformamide. The washed particles were dispersed in 700 mL of N,N-dimethylformamide using the ultrasonic probe (amplitude 70%, 30 minutes, pulse rate: 1 s on, 0.5 s off).

Immediately before using the solid composite materials for synthesis, the ferrofluid was dispersed again using the ultrasonic probe (amplitude 70%, 15 minutes, pulse rate: 1 s on, 0.5 s off).

Solid Residue

To determine the solid residue, 46.978 g of the freshly dispersed ferrofluid was evaporated in a beaker to complete dryness at 150° C. and subsequently dried in the drying cabinet for 30 minutes at 160° C. After drying 1.183 g of solid remains.

II. Preparation of the Composite Material

To prepare the composite materials K1 to K47 according to Table 5, the production method and the indicated amount of chemicals (in gram, unless otherwise specified) indicated in the table were used for each composite material.

TABLE 1

Synthesis of the composite material

| Composite Material | Ferrofluid | Monomer A1 | A2-1 | A2-2 | A2-3 | A2-4 | A2-5 | A2-6 | A2-7 | Surfactant T-1 | T-2 |
|---|---|---|---|---|---|---|---|---|---|---|---|
| K1  | F1 | 0.738 | 0.60 | — | — | — | — | 0.378 | — | 11.0 | — |
| K2  | F1 | 0.939 | — | — | — | — | — | 0.378 | — | 11.0 | — |
| K3  | F1 | 0.939 | — | — | — | — | — | — | 0.276 | 11.0 | — |
| K4  | F1 | 0.939 | — | — | — | — | — | 0.378 | — | 11.0 | — |
| K5  | F1 | 0.939 | — | — | — | — | — | 0.378 | — | 11.0 | — |
| K6  | F1 | 0.738 | 0.60 | — | — | — | — | 0.378 | — | 11.0 | — |
| K7  | F1 | 1,.341 | 1.80 | — | — | — | — | 0.252 | — | 11.0 | — |
| K8  | F1 | 1.341 | 1.80 | — | — | — | — | 0.252 | — | 11.0 | — |
| K9  | F1 | 1.341 | 1.80 | — | — | — | — | 0.252 | — | 11.0 | — |
| K10 | F1 | 1.341 | 1.80 | — | — | — | — | 0.252 | — | 11.0 | — |
| K11 | F2 | 1.341 | 1.80 | — | — | — | — | 0.252 | — | 11.0 | — |
| K12 | F1 | 1.341 | 1.80 | — | — | — | — | 0.252 | — | — | — |
| K13 | F2 | 1.341 | 1.80 | — | — | — | — | 0.252 | — | — | — |
| K14 | F1 | 2.012 | 2.00 | — | — | — | — | 0.315 | — | 11.0 | — |
| K15 | F2 | 2.012 | 2.00 | — | — | — | — | 0.315 | — | 11.0 | — |
| K16 | F1 | 2.012 | — | 0.451 | — | — | — | 0.315 | — | 11.0 | — |
| K17 | F2 | 2.012 | — | 0.451 | — | — | — | 0.315 | — | 11.0 | — |
| K18 | F1 | 2.012 | 2.00 | — | — | — | — | 0.315 | — | 11.0 | — |
| K19 | F2 | 2.012 | 2.00 | — | — | — | — | 0.315 | — | 11.0 | — |
| K20 | F1 | 2.012 | — | — | 12.50 | — | — | 0.315 | — | 11.0 | — |
| K21 | F2 | 2.012 | — | — | 12.50 | — | — | 0.315 | — | 11.0 | — |
| K22 | F1 | 2.012 | — | 0.360 | 2.50 | — | — | 0.315 | — | 11.0 | — |
| K23 | F2 | 2.012 | — | 0.360 | 2.50 | — | — | 0.315 | — | 11.0 | — |
| K24 | F1 | 2.012 | 2.00 | — | — | — | — | 0.315 | — | 20.0 | — |
| K25 | F1 | 2.012 | 2.00 | — | — | — | — | 0.315 | — | 30.0 | — |
| K26 | F2 | 2.012 | 2.00 | — | — | — | — | 0.315 | — | 20.0 | — |
| K27 | F2 | 2.012 | 2.00 | — | — | — | — | 0.315 | — | 30.0 | — |
| K28 | F1 | 2.012 | 2.00 | — | — | — | — | 0.315 | — | — | 11 g |
| K29 | F1 | 2.012 | 2.00 | — | — | — | — | 0.315 | — | — | 30 g |
| K30 | F1 | 2.012 | 2.00 | — | — | — | — | 0.315 | — | — | — |
| K31 | F1 | 2.012 | 2.00 | — | — | — | — | 0.315 | — | — | — |
| K32 | F1 | 2.012 | 2.00 | — | — | — | — | 0.315 | — | — | — |
| K33 | F1 | 2.012 | 2.00 | — | — | — | — | 0.315 | — | — | — |
| K34 | F1 | 2.012 | 2.00 | — | — | — | — | 0.315 | — | — | — |
| K35 | F1 | 2.012 | 2.00 | — | — | — | — | 0.315 | — | — | — |
| K36 | F1 | 2.012 | 1.00 (200) | — | — | — | — | 0.315 | — | 11.0 | — |
| K37 | F1 | 2.012 | 5.00 (1000) | — | — | — | — | 0.315 | — | 11.0 | — |
| K38 | F1 | 2.012 | — | — | — | 2.65 | — | 0.315 | — | 11.0 | — |
| K39 | F1 | 3.186 | — | — | — | — | — | — | — | 11.0 | — |
| K40 | F1 | 2.012 | 2.00 | — | — | — | — | 0.315 | — | 11.0 | — |
| K41 | F1 | 2.012 | 2.00 | — | — | — | — | 0.315 | — | 11.0 | — |
| K42 | F1 | 2.012 | 2.00 | — | — | — | — | 0.315 | — | 11.0 | — |
| K43 | F1 | 2.012 | 2.00 | — | — | — | — | 0.315 | — | 11.0 | — |
| K44 | F1 | 2.012 | 2.00 | — | — | — | — | 0.315 | — | — | — |
| K45 | F1 | 2.012 | — | — | — | — | 0.90 | 0.315 | — | 11.0 | — |
| K46 | F1 | 2.012 | — | — | — | — | 1.35 | 0.315 | — | 11.0 | — |
| K47 | F1 | 2.012 | 2.00 | — | — | — | — | 0.315 | — | 11.0 | — |

Synthesis of the composite material

| Composite Material | Surfactant T-3 | T-4 | T-5 | T-6 | Monomer B-1 | B-2 | B-3 | B-4 | Method | Stirring [rpm] | Reaction temperature & Emulsion temperature [° C.] | Duration |
|---|---|---|---|---|---|---|---|---|---|---|---|---|
| K1  | — | — | — | — | 2.874 | — | — | — | M1 | 580 | 60 | 48 h |
| K2  | — | — | — | — | 2.874 | — | — | — | M1 | 580 | 60 | 48 h |
| K3  | — | — | — | — | 2.874 | — | — | — | M1 | 580 | 60 | 48 h |
| K4  | — | — | — | — | — | — | 3.668 | — | M1 | 580 | 60 | 48 h |
| K5  | — | — | — | — | — | — | — | 2.775 | M1 | 580 | 60 | 22 h |
| K6  | — | — | — | — | 2.003 | — | — | 2.775 | M1 | 580 | 60 | 48 h |
| K7  | — | — | — | — | 4.354 | — | — | — | M1 | 210 | 60 | 72 h |
| K8  | — | — | — | — | — | — | 5.557 | — | M1 | 210 | 60 | 96 h |
| K9  | — | — | — | — | — | — | — | 4.,205 | M1 | 210 | 60 | 72 h |
| K10 | — | — | — | — | 4.354 | — | — | — | M1 | 210 | 60 | 72 h |
| K11 | — | — | — | — | 4.354 | — | — | — | M1 | 210 | 60 | 72 h |
| K12 | — | — | — | — | 4.354 | — | — | — | M1 | 210 | 60 | 96 h |
| K13 | — | — | — | — | 4.354 | — | — | — | M1 | 210 | 60 | 96 h |

TABLE 1-continued

| | | | | | | | | | | | | |
|---|---|---|---|---|---|---|---|---|---|---|---|---|
| K14 | — | — | — | — | 3.483 | — | — | — | M1 | 210 | 60 | 96 h |
| K15 | — | — | — | — | 3.483 | — | — | — | M1 | 210 | 60 | 96 h |
| K16 | — | — | — | — | 3.483 | — | — | — | M1 | 210 | 60 | 72 h |
| K17 | — | — | — | — | 3.483 | — | — | — | M1 | 210 | 60 | 72 h |
| K18 | — | — | — | — | — | 3.483 | — | — | M1 | 210 | 60 | 96 h |
| K19 | — | — | — | — | — | 3.483 | — | — | M1 | 210 | 60 | 96 h |
| K20 | — | — | — | — | 3.483 | — | — | — | M1 | 210 | 60 | 72 h |
| K21 | — | — | — | — | 3.483 | — | — | — | M1 | 210 | 60 | 72 h |
| K22 | — | — | — | — | 3.483 | — | — | — | M1 | 210 | 60 | 96 h |
| K23 | — | — | — | — | 3.483 | — | — | — | M1 | 210 | 60 | 96 h |
| K24 | — | — | — | — | — | 3.483 | — | — | M1 | 210 | 60 | 96 h |
| K25 | — | — | — | — | — | 3.483 | — | — | M1 | 210 | 60 | 96 h |
| K26 | — | — | — | — | — | 3.483 | — | — | M1 | 210 | 60 | 72 h |
| K27 | — | — | — | — | — | 3.483 | — | — | M1 | 210 | 60 | 72 h |
| K28 | — | — | — | — | — | 3.483 | — | — | M1 | 210 | 60 | 72 h |
| K29 | — | — | — | — | — | 3.483 | — | — | M1 | 210 | 60 | 72 h |
| K30 | 11 g | — | — | — | — | 3.483 | — | — | M1 | 210 | 60 | 96 h |
| K31 | 30 g | — | — | — | — | 3.483 | — | — | M1 | 210 | 60 | 96 h |
| K32 | — | 11 g | — | — | — | 3.483 | — | — | M1 | 210 | 60 | 72 h |
| K33 | — | 30 g | — | — | — | 3.483 | — | — | M1 | 210 | 60 | 72 h |
| K34 | — | — | 11 g | — | — | 3.483 | — | — | M1 | 210 | 60 | 96 h |
| K35 | — | — | 30 g | — | — | 3.483 | — | — | M1 | 210 | 60 | 96 h |
| K36 | — | — | — | — | 3.486 | — | — | — | M1 | 210 | 60 | 72 h |
| K37 | — | — | — | — | 3.483 | — | — | — | M1 | 210 | 60 | 72 h |
| K38 | — | — | — | — | 3.483 | — | — | — | M1 | 210 | 60 | 96 h |
| K39 | — | — | — | — | 3.483 | — | — | — | M1 | 210 | 60 | 96 h |
| K40 | — | — | — | — | 3.483 | — | — | — | M1 | 210 | 40 | 72 h |
| K41 | — | — | — | — | 3.483 | — | — | — | M1 | 210 | 50 | 72 h |
| K42 | — | — | — | — | 3.483 | — | — | — | M1 | 210 | 70 | 96 h |
| K43 | — | — | — | — | 3.483 | — | — | — | M1 | 210 | 80 | 96 h |
| K44 | — | — | — | 11 g | 3.483 | — | — | — | M1 | 210 | 60 | 72 h |
| K45 | — | — | — | — | — | 4.354 | — | — | M1 | 210 | 60 | 72 h |
| K46 | — | — | — | — | — | 5.225 | — | — | M1 | 210 | 60 | 72 h |
| K47 | — | — | — | — | — | 3.483 | — | — | M2 | 210 | 60 | 72 h |

Table 5 lists the amounts of chemicals used in gram, unless otherwise specified.
The Following Chemicals were Used:
Iron(II) chloride hexahydrate (Fisher Chemical, >97%)
Iron(II) chloride tetrahydrate (Sigma-Aldrich, puriss, ≥99.0%)
Ammonium hydroxide solution (Sigma-Aldrich, puriss, ~25%)
Sodium citrate dihydrate (Sigma-Aldrich, ≥99%)
N,N-Dimethylformamide (VWR, 99.9%)
1,4-Diazabicyclo[2.2.2]octane (Sigma-Aldrich, ReagentPlus®, ≥99%)
Cyclohexane (Bernd Kraft, min. 98%)
White oil WX32 (Addinol Lube Oil GmbH, medical white oil)
Ethanol (Bernd Kraft, 99%, denatured)
Monomer A1: 2,2-Bis(hydroxymethyl)propionic acid (Sigma-Aldrich, 98%)
Monomer A2-1: Polyethylene glycol (Mn=400 g/mol, Sigma-Aldrich), average molar mass otherwise indicated with amount (200)=Mn=200 g/mol;

(1,000)=Mn=1000 g/mol (Sigma-Aldrich, respectively)

Monomer A2-2: 1,4-Butanediol (Sigma-Aldrich, 99%)
Monomer A2-3: Poly[di(ethylene glycol)adipate] ($M_n$~2500 g/mol, Sigma-Aldrich)
Monomer A2-4: Polycaprolactone diol ($M_n$~530 g/mol, Sigma-Aldrich)
Monomer A2-5: 1,3-Dihydroxyacetone dimer (Sigma-Aldrich, 97%)
Monomer A2-6: 1,3,5-Trihydroxybenzene (Sigma-Aldrich, ≥99%)
Monomer A2-7: Glycerol (Sigma-Aldrich, ≥99.5%)
Monomer B-1: Toluene-2,4-diisocyanate (Sigma-Aldrich, ≥98.0%)
Monomer B-2: Lupranate T 80 (Sigma-Aldrich)
Monomer B-3 Isophorone diisocyanate (Sigma-Aldrich, 98%)
Monomer B-4 Hexamethylene diisocyanate (Sigma-Aldrich, ≥98.0%)
Surfactant T-1: Span 80 (Merck, for synthesis)
Surfactant T-2: Span 65 (Sigma-Aldrich)
Surfactant T-3: Span 60 (Sigma-Aldrich)
Surfactant T-4: Span 83 (TCI)
Surfactant T-5: Span 85 (Sigma-Aldrich)
Surfactant T-6: Brij 52 ($M_n$~330 g/mol, Sigma-Aldrich)
Preparation Methods According to Table 5:

The particulate solid composite materials were synthesized in a 1 L reaction vessel composed of a flat flange round flask (1 L/NW100 with groove) and a flanged flange cover (NW 100) with 4 joints (middle neck sleeve NS 29, 2× lateral sleeve NS 29 oblique, 1× lateral sleeve NS 14,5 vertical), an o-ring (silicone, NW 100) and a fast-action closure (NW 100). A KPG stirrer was used as stirrer (Heidolph, model RZR 2102 control) with a three blade propeller stirrer (VWR, cat. no.: BOHLC378-20, shaft diameter 10 mm, shaft length 600 mm, stirrer diameter 75 mm), which was introduced into the reaction vessel through the middle neck joint. The temperature of the reaction vessel was controlled by an oil bath with hot plate.
Method M1:

In a 1 L reaction vessel, 395 mL of cyclohexane was added to 50 mL of the ferrofluid specified in Table 5, 5 mL of N,N-dimethylformamide, the indicated amounts of monomers A, 0.1 g of 1,4-diazabicyclo[2.2.2]octane and, if present, the specified amount of surfactant and stirred for 60 minutes at the emulsification temperature specified in Table 5 and at the stir rate specified in Table 5. The amount of monomer B in 5 mL of cyclohexane specified in Table 5 was added under stirring at the abovementioned temperature.

The mixture was stirred for the specified reaction time at the specified reaction temperature. The particles were separated using a NdFeB magnet and washed twice with ethanol, twice with acetone, and five times with water.

Method M2:

In a 1 L reaction vessel, 395 mL of white oil WX32 was added to 50 mL of the ferrofluid specified in Table 5, 5 mL of N,N-dimethylformamide, the indicated amounts of monomers A, 0.1 g of 1,4-diazabicydo[2.2.2]octane and, if present, the indicated amount of surfactant and stirred for 60 minutes at the emulsification temperature specified in Table 5 and at the stir rate specified in Table 5. The amount of monomer B in 5 mL of white oil WX32 specified in Table 5 was added under stirring at the abovementioned temperature. The mixture was stirred for the specified reaction time at the specified reaction temperature. The particles were separated using an NdFeB magnet and washed twice with ethanol, twice with acetone, and five times with water.

III. Analysis of the Composite Materials

The average particle diameter of the composite materials prepared in Point II and the amount of embedded magnetic nanopartides was determined. The values were summarized in Table 6.

Determination of the Average Particle Diameter:

The particle sizes and particle distributions were determined and analyzed using a Beckman Multisizer™ 3 Coulter Counter® (Software Beckman Coulter Multisizer™ 3, ©1990-2008, Version 3.53, Oct. 15, 2008, Beckman Coulter GmbH, Krefeld). For this purpose, one pinch (spatula tip) of the substance to be measured was added to 1 mL of DI water and the substance subsequently dispersed (2 minutes on the vortex mixer at 2,400 rpm (VELP Scientifica ZX4 Advanced IR Vortex Mixer, VELP Scientifica Sri, Italy) and 2 minutes in the ultrasonic bath (VWR, USC300T, 80 W)). 200 µL of this suspension were removed and admixed with 5 mL of a 10% Triton solution (Triton X-100 high purity, Carl Roth GmbH & Co. K G) and homogenized (1 minute on the vortex mixer at 2,400 rpm (VELP Scientifica ZX4 Advanced IR Vortex Mixer, VELP Scientifica Sri, Italy)). Of the solutions prepared in this way, 1 mL was added to 150 mL of the isotonic solution in the Coulter (Coulter Isoton II Diluent, item no. 8546719, Beckman Coulter GmbH, Krefeld). The measurements were performed according to the manufacturer's instructions. The average particle diameters indicated in each reaction example are the volume averaged particle diameters reported by the instrument software. According to the Coulter principal, the particle volume is converted to a particle diameter. This particle diameter corresponds to the equivalent diameter, i.e., the diameter of a sphere the volume of which corresponds to the particle volume. The Coulter measurement principle is based on employing a capillary tube with an aperture. Each aperture is suitable to record particles that are within the range of 2 to 60% of the aperture diameter. Typical aperture diameters are in the range of 20 to 2000 µm. For example, a 30-µm aperture is therefore suitable to record particles within the range of 0.6 to 18 µm. In order to determine the particle sizes in the different reaction examples, different apertures were therefore required.

The specification of the average particle diameters are indicated in Table 6 with respect to the aperture used for the respective measurement (aperture: 20 µm (*), 30 µm (), 70 µm (*), 140 µm (**), 280 µm (*), 400 µm (****)).

Determination of the Iron Oxide Amount

This determination serves as a measure for the proportion of magnetic nanoparticles present in the composite material. In order to determine the amount of solid material, duplicate measurements with approximately 500 mg of substance were performed in each case. For this purpose, the samples were pre-dried for 2 hours at 120° C. and cooled down to room temperature again. The samples were subjected to a controlled temperature program (570 minutes temperature ramp from 0° C. to 950° C., 120 minutes 950° C.), cooled down to temperature, and the weight difference before and after the temperature treatment was determined. The indicated values are the averages of the results from both measurements.

Transmission Electron Microscopic Figures

Figure 2:
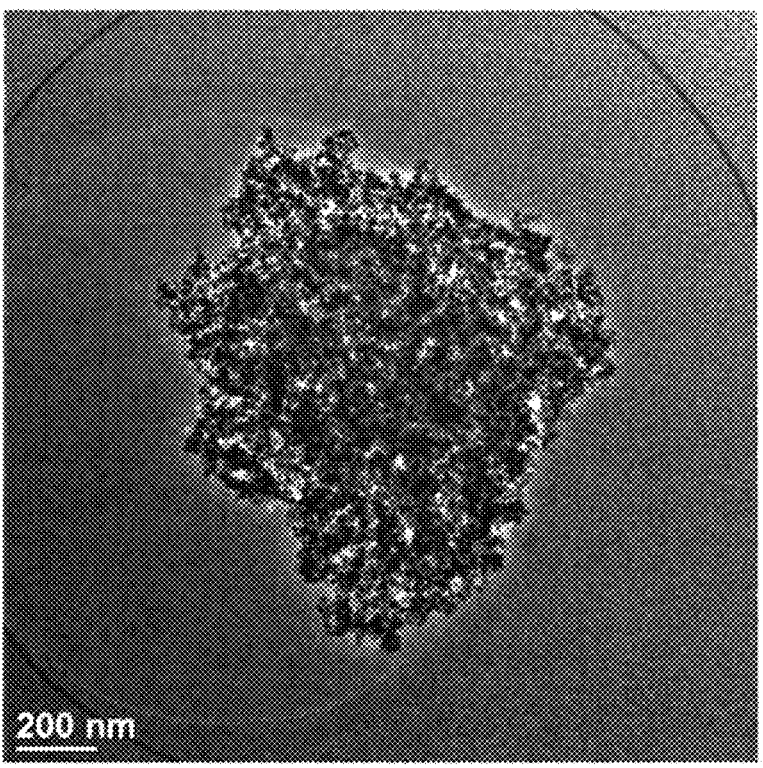

Transmission electron microscopic figures (FIG. 1 & FIG. 2) were generated using a CM300 UT FEG from FEI (formerly Philips) with 297 kV accelerating voltage and a 2 k×2 k MSC-CCD camera. For each test, one pinch (spatula tip) of the substance to be investigated was dispersed in 5 mL of absolute ethanol for 2 minutes in an ultrasonic bath (VWR, USC300T, 80 W), one drop of the suspension was applied to a Quantifoil TEM grid (200-mesh copper grid with a carbon hole film, R1.2/1.3) and the grid was air-dried for 10 minutes.

TABLE 6

Analysis results of the composite material

| Composite material | Average particle size [µm] | Iron oxide content [wt %] |
|---|---|---|
| K1 | 2.17 ** | — |
| K2 | 1.54 ** | — |
| K3 | 1.73 ** (see FIG. 1) | — |
| K4 | 0.87 ** | — |
| K5 | 28.01 ****** | — |
| K6 | 1.00 ** (see FIG .2) | — |
| K7 | 1.26 * | 66.3 |
| K8 | 1.34 ** | — |
| K9 | 30.03 ***** | — |
| K10 | 1.17 * | 70.4 |
| K11 | 1.02 ** | — |
| K12 | 1.28 * | 76.1 |
| K13 | 4.43 *** | — |
| K14 | 1.03 ** | 87.5 |
| K15 | 1.06 ** | — |
| K16 | 1.00 ** | — |
| K17 | 2.47 * | — |
| K18 | 0.93 * | 85.4 |
| K19 | 1.42 ** | — |
| K20 | 2.80 ** | — |
| K21 | 2.51 *** | — |
| K22 | 0.87 ** | 86.8 |
| K23 | 1.22 ** | — |
| K24 | 0.98 ** | — |
| K25 | 0.78 * | 89.5 |
| K26 | 1.32 ** | — |
| K27 | 1.54 ** | — |
| K28 | 1.18 ** | — |
| K29 | 1.19 ** | — |
| K30 | 1.92 *** | — |
| K31 | 3.50 *** | — |
| K32 | 1.06 ** | — |
| K33 | 13.19 *** | — |
| K34 | 1.24 ** | — |
| K35 | 1.18 ** | — |
| K36 | 0.98 ** | 88.0 |
| K37 | 1.07 ** | — |
| K38 | 1.00 ** | — |
| K39 | 0.97 ** | 98.7 |
| K40 | 0.95 ** | — |
| K41 | 0.96 ** | — |
| K42 | 1.00 ** | — |

TABLE 6-continued

Analysis results of the composite material

| Composite material | Average particle size [μm] | Iron oxide content [wt %] |
|---|---|---|
| K43 | 0.89 ** | — |
| K44 | 0.95 ** | — |
| K45 | 0.96 ** | — |
| K46 | 1.10 * | — |
| K47 | 0.92 ** | — |

(— = not determined)

IV. Purification of Nucleic Acids

Purification of Nucleic Acids Using Buffer System A:
Sample Preparation Magnetic Beads:

Sufficient amounts of washed magnetic beads from the reaction examples were added to a 2 mL SafeSeal microtube (Sarstedt, Nümbrecht), centrifuged using a laboratory centrifuge (Eppendorf centrifuge 5415 C, Fa. Eppendorf, Wesseling) for 2 minutes at 11,000 rpm, and the supernatant was pipetted off. Subsequently, 140 mg of magnetic beads were added to 1.5 mL Eppendorf-reaction tubes to which 1 mL ultrapure water (Millipore Direct-Q® 5 UV—R, ultrapure type 1, 0.8 μS/cm@25° C.) was added and the mixture dispersed (2 minutes Vortex mixer at 2,400 rpm (VELP Scientifica ZX4 Advanced IR Vortex Mixer, VELP Scientifica Sri, Italy) and 2 minutes in the ultrasonic bath (VWR, USC300T, 80W)).

Commercially available beads were used as reference for the beads according to the invention. These beads were taken from the NucleoMag® 96 Plant Kit (MACHEREY-NAGEL GmbH & Co. K G, Düren, Ref.-no. 744400.1, Kit-LOT: 1604/002). Said beads are NucleoMag® C-Beads with an average particle diameter of 2.29 μm. The NucleoMag® C-Bead solution was prepared in analogy to the procedure described for the magnetic beads in the reaction examples; therefore, the concentration of the C-Beads and the magnetic beads from the reaction examples were both 140 mg/mL in the solutions used.

Preparation Reference Lysate:

The buffers listed in the following are from the NucleoMag® 96 Plant Kit (MACHEREY-NAGEL GmbH & Co. K G, Düren, Ref.-no. 744400.1) and were used according to the manufacturer's instructions. For isolation of nucleic acids, leaf material from wheat germ was used as the sample material for a reference lysate. Corresponding amounts of leaf material were finely ground under liquid nitrogen using a mortar and pestle. The ground material was transferred to a 50 mL reaction tube, and the corresponding volumes of buffer MC1 were added (MACHEREY-NAGEL GmbH & Co. K G, Düren, Ref.-no. 744856.1) so that a concentration of 40 mg leaf material per 0.4 mL buffer solution was obtained. To this mixture was added 10 μL of a RNase A stock solution (c(RNase)=12 mg/mL per 40 mg leaf material, MACHEREY-NAGEL GmbH & Co. K G, Düren, Ref.-no. 744400.1). The stock solution was prepared by adding 1.25 mL ultrapure water to 15 mg lyophilized RNAse. The mixture was then lysed for 15 minutes at 65° C. Remaining solid components of the lysate mixture were separated by centrifugation in a tabletop centrifuge (Hettich Rotina 420R, 10 minutes at 4500×g).

Isolation of Nucleic Acids Using Buffer System A:

The isolation of nucleic acids was automated using a KingFisher™ Flex™ (Thermo Scientific Cat. no. 5400630, instrument software version 1.00.17, PC-Software Bindit, Version 3.3) in KingFisher™ Deep-well Blocks (KingFisher™ Accessory Kit B, MACHEREY-NAGEL GmbH & Co. K G, Düren, Ref.-Nr. 744951). KingFisher™ Elution Plates were used for elution. Further details and methods can be found in the KingFisher™ Flex™ Manual and the "User Guide for Automated purification of DNA from Plant leaves and seeds with KingFisher 96/KingFisher mL instrument and MACHEREY-NAGEL NucleoMag 96 Plant kit." Quadruple measurements were performed for each magnetic bead type in each reaction example.

30 μL bead solution and 400 μL buffer MC2 (MACHEREY-NAGEL GmbH & Co. K G, Düren, Ref.-no. 744857.1) was added to 400 μL of the respective lysate. The mixture was mixed for 5 minutes at room temperature on the KingFisher™ Flex™ by moving the tip combs up and down (96 DW tip comb, KingFisher™ Accessory Kit B, MACHEREY-NAGEL GmbH & Co. K G, Düren, Ref.-no. 744951, mixing speed "half mix"), and the beads were then magnetically separated for 2 minutes by moving the magnet tips into the tip combs. The magnetic beads deposited on the tip combs and the nucleic acids bonded to the beads were transferred to another KingFisher™ Deep-well Block, the cavities of which were each filled with 600 μL wash buffer 1 (MC3, MACHEREY-NAGEL GmbH & Co. K G, Düren, Ref.-no. 744858.1). By drawing out the magnet tips, the magnetic beads were released and mixed by moving the tip combs up and down for 1 minute at room temperature (mixing speed "half mix"). The magnetic beads were then magnetically separated for 2 minutes by moving the magnet tips into the tip combs and transferred to another KingFisher™ Deep-well Block, the cavities of which were each filled with 600 μL wash buffer 2 (MC4, MACHEREY-NAGEL GmbH & Co. K G, Düren, Ref.-no. 744859.1). The magnetic beads were released using the conditions described for wash buffer 1, suspended, separated again, and transferred to another Deep-well Block, the cavities of which were each filled with 600 μL wash buffer 3 (80% ethanol). The magnetic beads were dispersed by drawing out the magnet tips and moving the comb tips up and down (mixing speed "fast") for 1 minute at room temperature. The magnet tips were moved into the tip combs again, the magnetic beads magnetically separated for 2 minutes and transferred to another KingFisher™ Deep-well Block, the cavities of which were each filled with 600 μL wash buffer 4 (MC4, MACHEREY-NAGEL GmbH & Co. K G, Düren, Ref.-no. 744860.1). The beads were incubated for 1 minute at room temperature with drawn in magnet tips without a resuspension step, and then transferred to a KingFisher™ Elution Plate, the cavities of which were each filled with 100 μL elution buffer (MC6, MACHEREY-NAGEL GmbH & Co. K G, Düren, Ref.-no. 744861.1). The beads were resuspended at 55° C. by drawing out the magnet tips followed by moving the tip combs up and down (15 s "fast", 2 min 15 s "slow"). By drawing in the magnet tips, the beads were magnetically separated for 5 minutes and removed from the eluates by drawing out the tip combs. The KingFisher™ Elution Plate was removed from the KingFisher™ Flex™ and transferred to a NudeoMag® Separator (NudeoMag® SEP, MACHEREY-NAGEL GmbH & Co. K G, Düren, Ref.-no. 744900) in order to separate any residual beads that may have still been present. The respective eluates were subsequently removed and used as described below.

Analysis of the Eluates:

The eluates were analyzed by spectrophotometry using a microplate spectrophotometer (BioTek Synergy HT, BioTek Instruments, Inc., Winooski, USA) and appropriate compatible UV measurement plates (UV-Star® Microplate 96 well, Greiner Bio-One GmbH, Cat.-No. 655801), as well as by agarose gel electrophoresis. The Lambda DNA/HindIII Marker 2 (Thermo Fisher Scientific, Cat.-no. SM0101) was used as the size standard for agarose gel electrophoresis. 3 µL sample buffer (6×DNA Loading Dye from the above Thermo Fisher Scientific Kit) were added to 15 µL of each eluate from the reaction examples and electrophoretically separated in a 0.7% agarose gel at 90 V for 30 minutes. The nucleic acid were detected using ethidium bromide under UV light and using INTAS photo documentation with the INTAS GDS Software.

To test the suitability of the isolated nucleic acids for use in subsequent applications, amplifications were performed using TaqMan-PCR on the Applied Biosystems® HID 7500 Real Time PCR System (with HID Real-Time PCR Analysis Software v1.1, @2010 Life Technologies Corporation). To this end, 2 µL of the eluates were mixed with 18 µL of a PCR master mix (SensiFast™ Probe LoRox Kit, Bioline USA Inc., Taunton, Cat.-no. BIO-84002, with Primer A (sequence: 5'-CAA GCA GCA TGA AGA TCA AGG T-3', concentration 10 pmol/µL), Primer B (sequence: 5'-CAC ATC TGT TGG AAA GTG CTG AG-3', concentration 10 pmol/µL), probe ((FAM)-CCT CCA ATC CAG ACA CTG TAC TTY CTC TC-(TAMRA), concentration 10 pmol/µL with FAM=6-carboxyfluorescein and TAMRA=tetramethylrhodamine)) in MicroAMP® Optical 96-Well Reaction plates (Thermo Fisher Scientific, Cat.-no. N8010560) and covered with MicroAMP® Optical Adhesive Film (Thermo Fisher Scientific, Cat.-no. 4360954). PCR was performed using the following instrument settings: 95° C. 5 minutes, 40× cycles with 10 seconds 95° C. and 1 minute 60° C.

Isolation of Nucleic Acids Using Buffer System B:
Sample Preparation Magnetic Beads:

In order to isolate nucleic acids, 5 magnetic beads from the reaction examples (K3, K8, K34, K46 and K47) were used in combination with a different buffer system. To this end, the magnetic beads were provided in dispersed form in an aqueous solution according to the aforedescribed preparation steps. As a reference, NucleoMag® C-Beads from the NudeoMag® 96 Plant Kit (MACHEREY-NAGEL GmbH & Co. K G, Düren, Ref.-no. 744400.1, Kit-LOT: 1604/002) with an average particle diameter of 2.29 µm and M-PVA C21 Beads (PerkinElmer chemagen Technologie GmbH, Baesweiler, Prod.-no. CMG-206, LOT-no. C21-0108015) with a particle diameter in the range between 0.5-1.25 µm (includes >95.0% of all particles). The NucleoMag® C-Bead solution and the M-PVA C21 Bead solution were also prepared according to the reaction examples (140 mg/mL).

Preparation Reference Lysate:

For isolation of nucleic acids, leaf material from wheat germ was used as the sample material for a reference lysate. To this end, appropriate amounts of the leaf material was finely crushed under liquid nitrogen using a mortar and pestle. 35 mL lysis buffer (200 mM Tris-HCl, 250 mM NaCl, 25 mM EDTA, 0.5% SDS, pH=8) and 700 µL RNase A stock solution (c(RNase)=12 mg/mL, MACHEREY-NAGEL GmbH & Co. K G, Düren, Ref.-no. 744400.1) was added to 2.8 g of the leaf material. The stock solution was prepared by adding 2.5 mL ultrapure water to 30 mg lyophilized RNAse. The mixture was then lysed for 30 minutes at 56° C. Remaining solid components of the lysate mixture were separated by centrifugation in a tabletop centrifuge (Hettich Rotina 420R, 10 minutes at 4500×g).

Isolation of Nucleic Acids Using Buffer System B:

Automated isolation of the nucleic acids was performed on a KingFisher™ Flex™ according to the previous examples on isolation of nucleic acids. Quadruple measurements were performed for each bead type for the selected reaction examples.

30 µL bead solution and 400 µL binding buffer (isopropanol) were added to 400 µL of the lysate. The mixture was mixed for 5 minutes at room temperature on the KingFisher™ Flex™ by moving the tip combs up and down (96 DW tip comb, KingFisher™ Accessory Kit B, MACHEREY-NAGEL GmbH & Co. K G, Düren, Ref.-no. 744951, mixing speed "half mix"), and the beads were then magnetically separated for 2 minutes by moving the magnet tips into the tip combs.

The magnetic beads deposited on the tip combs and the nucleic acids bonded to the beads were transferred to another KingFisher™ Deep-well Block, the cavities of which were each filled with 600 µL wash buffer 1 (2.2 M guanidine hydrochloride, 70% ethanol, 10 mM Tris, pH=6.5). By drawing out the magnet tips, the magnetic beads were released and mixed by moving the tip combs up and down for 1 minute at room temperature (mixing speed "half mix").

The magnetic beads were then magnetically separated for 2 minutes by moving the magnet tips into the tip combs and transferred to another KingFisher™ Deep-well Block, the cavities of which were each filled with 600 µL wash buffer 2 (80% ethanol). The magnetic beads were released using the conditions described for wash buffer 1, suspended, separated again, and transferred to another Deep-well Block, the cavities of which were each filled with 600 µL wash buffer 3 (80% ethanol). The magnetic beads were dispersed by drawing out the magnet tips and moving the comb tips up and down (mixing speed "fast") for 1 minute at room temperature. The magnet tips were moved back into the tip combs, the magnetic beads magnetically separated for 2 minutes and transferred to a KingFisher™ Elution Plate, the cavities of which were each filled with 125 µL elution buffer (5 mM Tris-HCl, pH=8.5). The beads were resuspended at 55° C. by drawing out the magnet tips, followed by moving the tip combs up and down (15 s "fast", 2 min 15 s "slow") at 55° C. By drawing in the magnet tips, the beads were magnetically separated for 5 minutes and removed from the eluates by moving out the tip combs.

The KingFisher™ Elution Plate was removed from the KingFisher™ Flex™ and transferred to a NudeoMag® Separator (NucleoMag® SEP, MACHEREY-NAGEL GmbH & Co. K G, Düren, Ref.-no. 744900) in order to separate any residual beads that may have still been present. The respective eluates were subsequently removed and used as described below.

Analysis of the Eluates:

The eluates were analyzed by spectrophotometry using a microplate spectrophotometer (BioTek Synergy HT, BioTek Instruments, Inc., Winooski, USA) according to the previous reaction examples and with appropriate compatible UV measurement plates (UV-Star® Microplate 96 well, Greiner Bio-One GmbH, Cat.-No. 655801) as well as by agarose gel electrophoresis. The Lambda DNA/HindIII Marker 2 (Thermo Fisher Scientific, Cat.-no. SM0101) was used as the size standard for agarose gel electrophoresis. 3 µL sample buffer (6×DNA Loading Dye from the above Thermo Fisher Scientific Kit) were added to 15 µL of each eluate from the reaction examples and electrophoretic dearly separated in a 0.7% agarose gel at 90 V for 30 minutes. The nucleic acid were detected using ethidium bromide under UV light and using INTAS photo documentation with the INTAS GDS Software.

3. Results

The properties of the magnetic composite material plays a crucial role with respect to its usability for the individual method steps. The properties to be named in this respect are mainly a fast and homogeneous dispersability of the magnetic beads in the various media, a flow behavior of the various solutions containing the different magnetic beads that does not leave residues on pipette and vessel walls, fast magnetic separability, and the slowest possible sedimentation behavior of the magnetic beads in the respective solutions.

Figure 3:
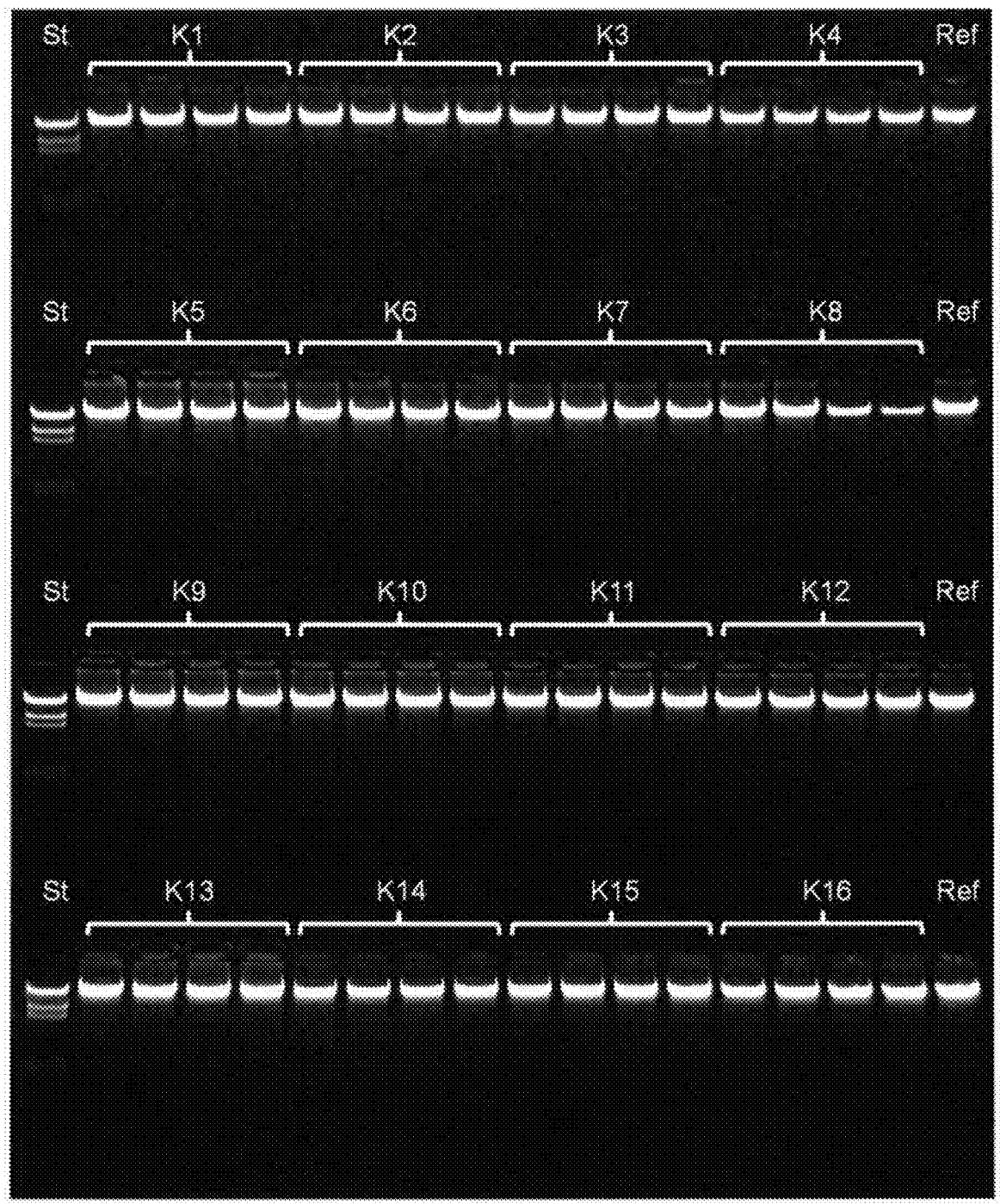
FIGS. 3, 4, and 5 show isolated nucleic acids isolated using the beads from reaction examples.
Figure 4:
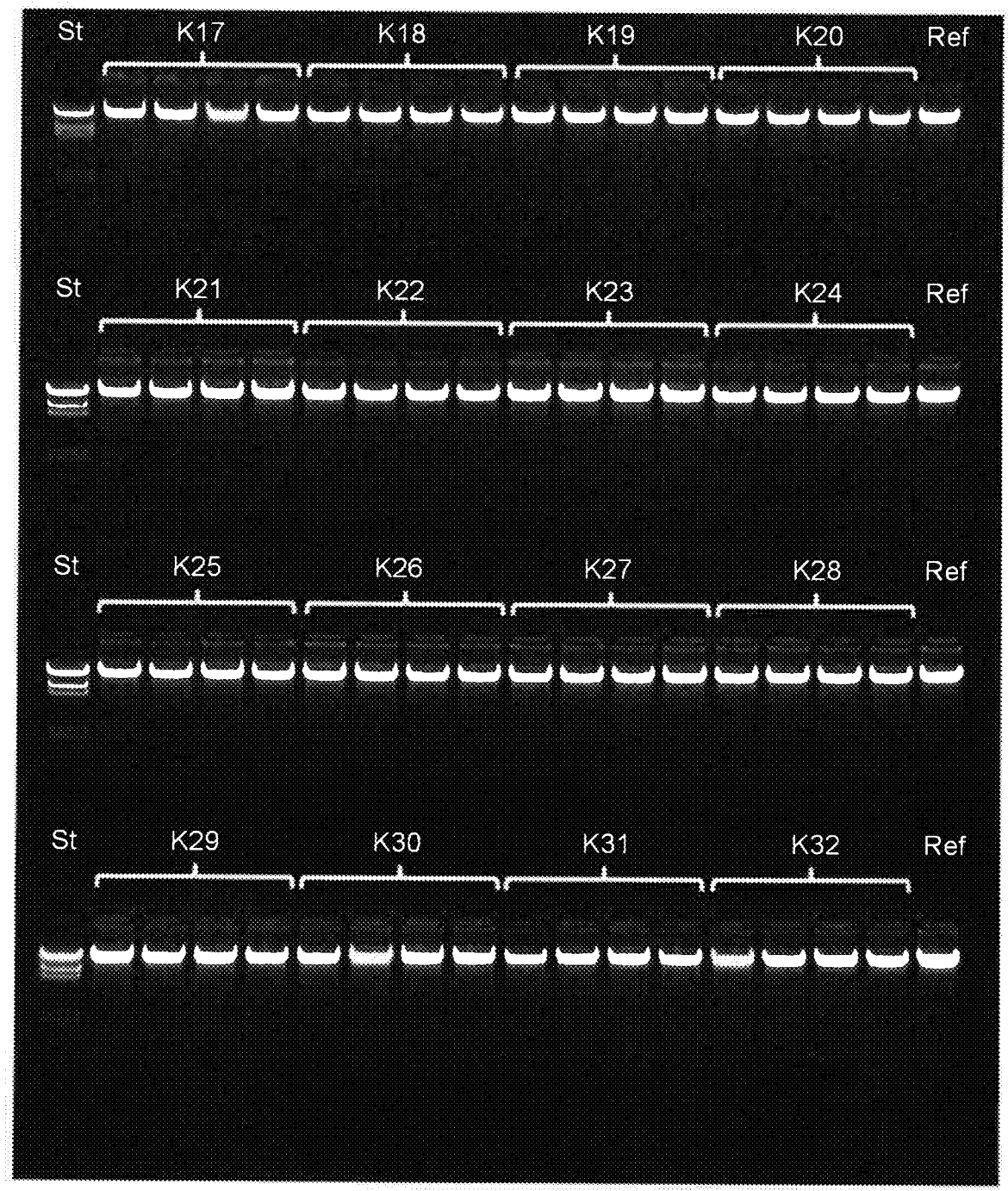
Figure 5:
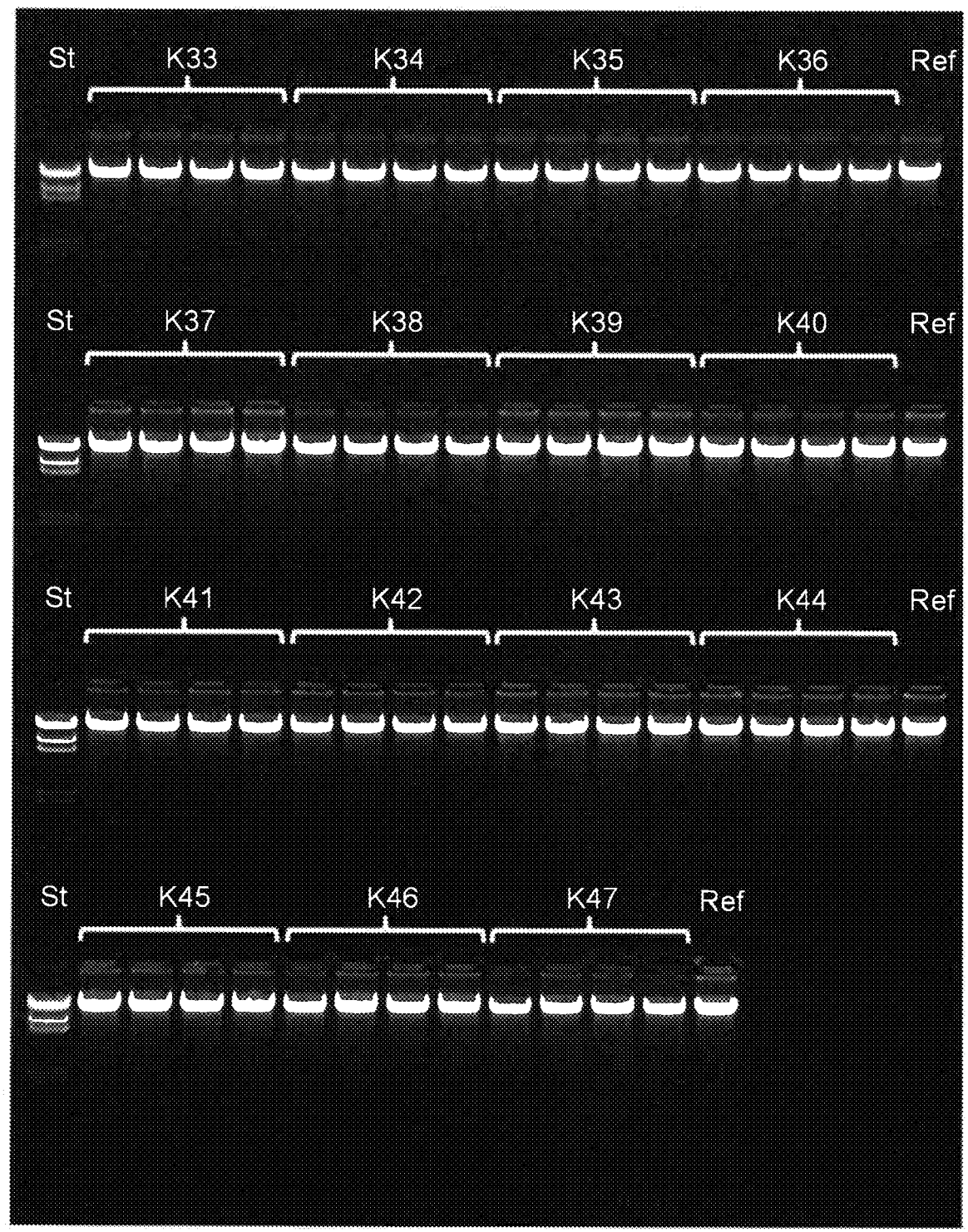

The magnetic beads according to the invention could be used to isolate nucleic acids using the described automated method and therefore displayed said properties. For almost all of the samples examined, the spectrophotometric examination of the eluates with respect to nucleic acid content revealed a binding amount of nucleic acids that was comparable with the reference. The gel electrophoretic separation that was performed on eluates obtained from wheat show the isolated nucleic acids isolated using the beads from the respective reaction examples (FIGS. 3, 4, and 5). Differences in the quality of the purified nucleic acids were not observed; in each case the nucleic acids were non-graded and high molecular nucleic acids. The amounts of isolated nucleic acid are obviously within a range that is comparable to the amount of nucleic acids isolated using commercial beads.

Moreover, all of the nucleic acids isolated could be used in the subsequent PCR (polymerase chain reaction) application. The results of the PCR allowed to draw conclusions on the amount of nucleic acids that were initially present as well as on their purity with respect to contaminations that have inhibitory effects. The so-called Ct-value in the PCR describes the number of cycles required until the fluorescence signal has reached a threshold value, and thus indicates the start of the exponential amplification phase. When low amounts of isolated nucleic acids are present at the beginning of PCR, a high Ct value results, and when high amounts of isolated nucleic acids are present, a low Ct value results. However, this applies only when almost identical reaction conditions are used (e.g., type of nucleic acid, primers used, polymerase used) and in the absence of inhibitory effects. Inhibitory effects disrupt the amplification by delaying the amplification reaction, and therefore cause elevated Ct values even when a large amount of isolated nucleic acids are present. Inhibitory components may e.g., be nanoparticles that diffuse out of the beads.

The ΔCt is employed in order to better compare the results. It derives from the difference of the Ct value of the respective sample and the Ct-value of the reference sample ($\Delta Ct = Ct_{sample} - Ct_{reference}$). For PCR 4 eluates were used that were obtained using the inventive beads from the reaction examples or using the reference beads from the automated isolation method. The average value ($Ct_m$) was calculated from the 4 Ct values determined in this manner for each bead type. The $\Delta Ct_m$ value was calculated using these average values ($\Delta Ct_m = Ct_{m,sample} - Ct_{m,reference}$) and summarized for several reaction examples in the following Table 7:

TABLE 7

Average values of the $\Delta Ct_m$-values

| Reaction example | $\Delta Ct_m$ |
|---|---|
| K2 | −0.01 |
| K9 | 0.07 |
| K10 | 0.10 |
| K11 | 0.29 |
| K12 | 0.17 |
| K13 | −0.10 |
| K14 | 0.40 |
| K15 | 0.46 |
| K21 | 0.27 |
| K22 | 0.48 |
| K23 | 0.41 |
| K29 | 0.46 |
| K30 | 0.42 |
| K32 | 0.38 |
| K34 | 0.10 |
| K35 | 0.30 |
| K36 | 0.12 |
| K37 | 0.48 |
| K39 | 1.39 |
| K42 | 0.20 |
| K43 | 0.17 |
| K44 | 0.38 |
| K45 | −0.36 |
| K46 | −0.46 |

The majority of the values shown are in a range between −0.5 to +0.5 $\Delta Ct_m$. These differences are the result of slightly larger or smaller amounts of nucleic acid that was present at the beginning of the amplification reaction. Taking into account the figures, from which a comparable amount of isolated nucleic acid is apparent, using the inventive beads on the one hand, and the nucleic acids isolated using the reference beads on the other, the usability of the inventive beads for PCR is demonstrated without inhibitory effects occurring.

Of the values shown in Table 7, K39 shows a distinctly higher $\Delta Ct_m$-value. As, according to FIG. 5, the amount of isolated nucleic acid is comparable to the amount isolated using the reference beads, inhibitory interference is likely present. One reason for this can be eluting nanoparticles. As K39 was synthesized using only monomer A1 and without monomer A2 or A2a and/or A2b, this emphasizes the aforementioned significance of these monomers with respect to adjusting the embedding efficiency and encapsulation efficiency, among other factors.

Figure 6:
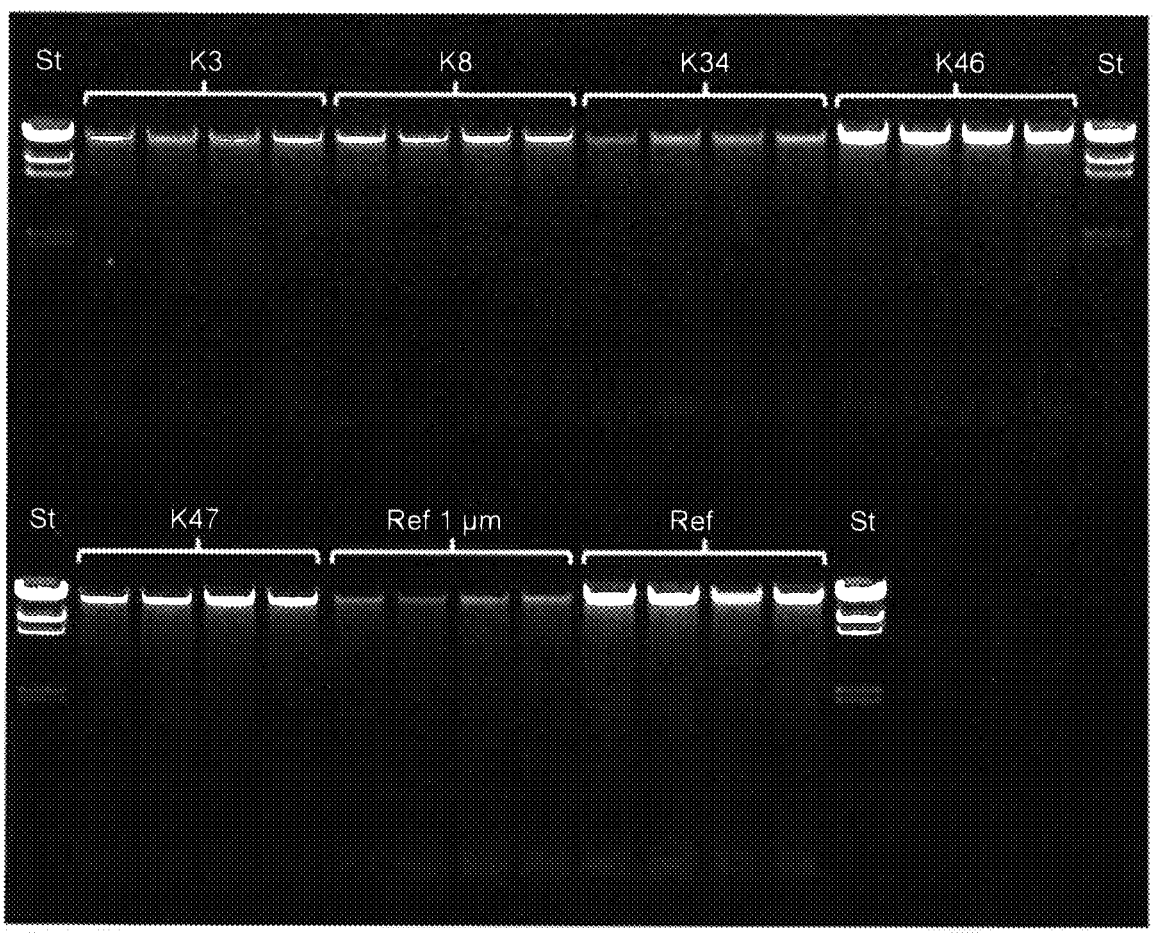
FIG. 6 shows the gel electrophoretic separation of the eluates that were obtained using buffer system B.

FIG. 6 shows the gel electrophoretic separation of the eluates that were obtained using buffer system B. The usability of the tested inventive beats for isolating nucleic acids was also given with this buffer system. Differences in the quality of the nucleic acids isolated and purified using the beads from the reaction examples and the reference beads were not observed; in each case, the nucleic acids were non-graded and high molecular nucleic acids.

The amounts of isolated nucleic acid are somewhat higher in K46 as compared to the amounts obtained using the NudeoMag® C-Beads (Ref), or, in the case of K3, K8, K34 and K47, the amounts are between the binding amounts achieved using the NucleoMag® C-Beads and the M-PVA C21 beads (Ref 1 μm). This shows that the usability of the inventive beads is not restricted to a specific buffer system and is comparable with commercially available products.

The invention claimed is:
1. A particulate solid composite material containing at least 40 wt % magnetic nanoparticles based on the particulate solid composite material embedded in a carrier matrix based on at least one polymer obtained by polyaddition, obtained using a method comprising the following steps
  a) providing a magnetic fluid in form of a suspension containing magnetic nanoparticles and a liquid continuous phase containing at least one polar organic liquid and less than 5 wt % of water, relative to the weight of the fluid,
  b) mixing the magnetic fluid with at least one isocyanate-reactive monomer A1, selected from compounds containing
    at least two functional groups each having at least one Zerewitinoff-reactive hydrogen atom, and
    in addition to these at least two functional groups, at least one anionic or potentially anionic residue,
  c) optionally adding at least one surfactant,
  d) emulsifying the mixture obtained in the previous steps in a liquid continuous phase, containing at least one nonpolar, organic liquid,
  e) adding at least one polyisocyanate monomer B,
  f) separating the formed composite material after the reaction time is completed and optionally washing,
with the proviso that the cLogP value (25° C.) of the polar organic liquid is smaller than the cLogP value (25° C.) of the nonpolar organic liquid, and the liquid, continuous phase from Step d) contains less than 5 wt % of water, relative to the weight of the continuous phase;
wherein the particulate solid composite material has an average particle size of from 0.5 µm to 250 µm.

2. A particulate solid composite material for nucleic acid purification, containing at least 40 wt % magnetic metal oxide nanoparticles based on the particulate solid composite material embedded in a carrier matrix containing more than 50% of at least one polymer that is obtained by polyaddition of
  a) at least one isocyanate-reactive monomer A, selected from compounds containing
    at least two functional groups each having at least one Zerewitinoff-reactive hydrogen atom, and,
    in addition to these at least two functional groups carries at least one anionic or potentially anionic residue,
  with
  b) at least one polyisocyanate monomer B, wherein the particulate solid composite material is produced by a method comprising:
  A) providing a magnetic fluid in form of a suspension containing the magnetic metal oxide nanoparticles and a liquid continuous phase containing at least one polar organic liquid and less than 5 wt % of water, relative to the weight of the fluid,
  B) mixing the magnetic fluid with the at least one isocyanate-reactive monomer A,
  C) optionally adding at least one surfactant,
  D) emulsifying the mixture obtained in the previous steps in a liquid continuous phase, containing at least one nonpolar, organic liquid,
  E) adding the at least one polyisocyanate monomer B,
  F) separating the formed composite material after the reaction time is completed and optionally washing,
with the proviso that said polyaddition occurs in the presence of the magnetic metal oxide nanoparticles;
wherein the particulate solid composite material has an average particle size of from 0.5 µm to 250 µm.

3. The particulate solid composite material according to claim 2, wherein the polymer of the carrier matrix is obtained by reaction of
  i) at least one isocyanate-reactive Monomer A, selected from compounds containing at least two functional groups, each carrying at least one Zerewitinoff-reactive hydrogen atom
  ii) at least one polyisocyanate monomer B
    by means of emulsion polymerization of an emulsion, containing
      i) in the discontinuous phase magnetic nanoparticles, at least one polar, organic liquid, having a cLogP value <1.5 (25° C.) and at least an isocyanate-reactive monomer A that differs from the polar, organic liquid, selected from compounds containing at least two functional groups each carrying at least one Zerewitinoff-reactive hydrogen atom, and
      ii) in the continuous phase at least one nonpolar, organic liquid,
    in the presence of polyisocyanate monomer B, with the proviso that the cLogP value (25° C.) of the polar organic liquid is smaller than the LogP value (25° C.) of the nonpolar, organic liquid.

4. The particulate solid composite material according to claim 2, wherein the magnetic metal oxide nanoparticles are magnetic iron oxide nanoparticles.

5. A kit for purifying nucleic acids comprising:
  a particulate solid composite material according to claim 2;
  and at least one additional component, selected from the group consisting of a user manual, binding buffer, wash buffer, and resuspension buffer for bringing the purified nucleic acids into solution.

6. A method for purification of nucleic acids from a nucleic acid-containing, biological sample, comprising the following steps:
  a) Providing an aqueous sample containing nucleic acids in solubilized form;
  b) Depositing at least nucleic acids from the aqueous sample onto a particulate solid composite material according to claim 2;
  c) Separating the nucleic acid-containing particulate solid composite material by applying a magnetic field, and optionally washing the separated particles with a wash solution;
  d) Bringing into solution the remaining nucleic acid from the particulate solid composite material treated according to Step c) using a resuspension buffer and separating the particulate solid composite material from the nucleic acid-containing solution.

7. A method for producing a particulate solid composite material for nucleic acid purification, containing at least 40 wt % magnetic nanoparticles based on the particulate solid composite material embedded in a carrier matrix based on at least one polymer obtained by polyaddition, wherein the method comprises the following steps
  a) providing a magnetic fluid in form of a suspension containing magnetic nanoparticles and a liquid continuous phase containing at least one polar organic liquid and less than 5 wt % of water, relative to the weight of the fluid,
  b) mixing the magnetic fluid with at least one isocyanate-reactive monomer A1, selected from compounds containing
    at least two functional groups each having at least one Zerewitinoff-reactive hydrogen atom, and
    in addition to these at least two functional groups, at least one anionic or potentially anionic residue, c) optionally adding at least one surfactant,
d) emulsifying the mixture obtained in the previous steps in a liquid continuous phase, containing at least one nonpolar, organic liquid,
e) adding at least one polyisocyanate monomer B,
f) separating the formed composite material after the reaction time is completed and optionally washing, with the proviso that the cLogP value (25° C.) of the polar organic liquid is smaller than the cLogP value (25° C.) of the nonpolar organic liquid, and the liquid, continuous phase from Step d) contains less than 5 wt % of water, relative to the weight of the continuous phase.

8. The method according to claim 7, wherein said polar, organic liquid has a cLogP value <1.5 (25° C.), and said nonpolar, organic liquid has a cLogP value >2.0 (25° C.).

9. The method according to claim 7, wherein the magnetic nanoparticles are selected from the group consisting of ferromagnetic nanoparticles, ferrimagnetic nanoparticles, and mixtures thereof.

10. The method according to claim 7, wherein the magnetic nanoparticles contain iron oxide.

11. The method according to claim 7, wherein the isocyanate-reactive monomer A1 is selected from the group consisting of 2,2-bis(hydroxymethyl)propionic acid, 2,3-diaminobenzoic acid, 2,4-diaminobenzoic acid, 2,5-diaminobenzoic acid, 2,6-diaminobenzoic acid, 3,4-diaminobenzoic acid, 3,5-diaminobenzoic acid, 2,2-bis(hydroxymethyl)acetic acid, 2,2,2-tri(hydroxymethyl)acetic acid, 2,2-bis(hydroxymethyl)propionic acid, 2,2-bis(hydroxymethyl)butyric acid, 2,2-bis(hydroxymethyl)pentanoic acid, 2,5-dihydroxy-3-methylpentanoic acid, 3,5-dihydroxy-3-methylpentanoic acid, 4,5-dihydroxy-3-methylpentanoic acid, 3,4-dihydroxy-3-methylpentanoic acid, 2,3-dihydroxy-3-methylpentanoic acid, 2,4-dihydroxy-3-methylpentanoic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid, 2,3-dihydroxysuccinic acid, 2,5-diaminopentanoic acid, 3,5-diaminopentanoic acid, 4,5-diaminopentanoic acid, 2,3-dihydroxybenzenesulfonic acid, 3,4-dihydroxybenzenesulfonic acid, 2,4-dihydroxybenzenelsulfonic acid, 2,5-dihydroxybenzene sulfonic acid, 3,5-dihydroxybenzenesulfonic acid, 2,3-diaminobenzenesulfonic acid, 3,4-diaminobenzenesulfonic acid, 2,4-diaminobenzenesulfonic acid, 2,5-diaminobenzenesulfonic acid, 3,5-diaminobenzenesulfonic acid, 3,4-dihydroxy-2-toluenesulfonic acid, 3,4-diamino-2-toluenesulfonic acid, 4,5-dihydroxy-2-toluenesulfonic acid, 4,5-diamino-2-toluenesulfonic acid, 5,6-dihydroxy-2-toluenesulfonic acid, 5,6-diamino-2-toluenesulfonic acid, 3,5-dihydroxy-2-toluenesulfonic acid, 3,5-diamino-2-toluenesulfonic acid, 3,6-dihydroxy-2-toluenesulfonic acid, 3,6-diamino-2-toluenesulfonic acid, 4,6-dihydroxy-2-toluenesulfonic acid, 4,6-diamino-2-toluenesulfonic acid, 2,4-dihydroxy-3-toluenesulfonic acid, 2,4-diamino-3-toluenesulfonic acid, 2,5-dihydroxy-3-toluenesulfonic acid, 2,5-diamino-3-toluenesulfonic acid, 2,6-dihydroxy-3-toluenesulfonic acid, 2,6-diamino-3-toluenesulfonic acid, 4,5-dihydroxy-3-toluenesulfonic acid, 4,5-diamino-3-toluenesulfonic acid, 4,6-dihydroxy-3-toluenesulfonic acid, 4,6-diamino-3-toluenesulfonic acid, 5,6-dihydroxy-3-toluenesulfonic acid, 5,6-diamino-3-toluenesulfonic acid, 2,3-dihydroxy-4-toluenesulfonic acid, 2,3-diamino-4-toluenesulfonic acid, 2,5-dihydroxy-4-toluenesulfonic acid, 2,5-diamino-4-toluenesulfonic acid, 2,6-dihydroxy-4-toluenesulfonic acid, 2,6-diamino-4-toluenesulfonic acid, 3,5-dihydroxy-4-toluenesulfonic acid, 3,5-diamino-4-toluenesulfonic acid, 3,6-dihydroxy-4-toluenesulfonic acid, 3,6-diamino-4-toluenesulfonic acid, 5,6-dihydroxy-4-toluenesulfonic acid, 5,6-diamino-4-toluenesulfonic acid, and combinations thereof.

12. The method according to claim 7, wherein, in addition to at least one monomer A1, at least one additional monomer A2 is used as isocyanate-reactive monomer, selected from non-ionic compounds containing at least two functional groups each carrying at least one Zerewitinoff-reactive hydrogen atom, whereby the isocyanate-reactive monomer A2
is selected from organic polyols, polyether polyols, polyester polyols, polycarbonate polyols, polyetherestercarbonate polyols, amino alcohols, organic polyamines, organic polyalkyleneamines, or combinations thereof, and/or
has a number average molecular weight Mn of from 200 g/mol to 10,000 g/mol, and/or
comprises a first isocyanate-reactive monomer A2a having two Zerewitinoff-reactive hydrogen atoms and a second isocyanate-reactive monomer A2b having three Zerewitinoff-reactive hydrogen atoms, whereby the first isocyanate-reactive monomer A2a is selected from compounds having two hydroxyl groups, amino groups, thiol groups, ketimine groups, ketazine groups, oxazolidine groups, or combinations thereof, and the second isocyanate-reactive monomer A2b is selected from compounds having three hydroxyl groups, amino groups, thiol groups, ketimine groups, ketazine groups, oxazolidine groups, or combinations thereof.

13. The method according to claim 7, wherein at least one non-ionic surfactant is added as surfactant in Step c).

14. The method according to claim 7, wherein the at least one polyisocyanate monomer B is selected from organic diisocyanates of the following formula (I),

O=C=N—R—N=C=O    (I)

wherein R represents a cycloaliphatic $C_{3-15}$ hydrocarbon residue, aromatic $C_{6-15}$ hydrocarbon residue, araliphatic $C_{6-18}$ hydrocarbon residue or aliphatic $C_{3-15}$ hydrocarbon residue.

15. The method according to claim 7, wherein the substance ratio between the amount of substance n(Zerewitinoff) of the functional groups having Zerewitinoff-active hydrogen atoms of all isocyanate reactive monomers used and the amount of substance n(NCO) of the isocyanate groups of all polyisocyanate monomers used is from 5:1 to 1:5.

16. The method according to claim 7, wherein:
the at least one anionic or potentially anionic residue is selected from the group consisting of carboxylate, sulfonate, and combinations thereof; and
wherein and the liquid, continuous phase from Step d) contains less than 2 wt % of water, relative to the weight of the continuous phase.

17. The method according to claim 7, wherein said polar, organic liquid has a cLogP value <1.0 (25° C.) and said nonpolar, organic liquid has a cLogP value >2.5 (25° C.).

18. The method according to claim 7, wherein the magnetic nanoparticles are selected from superparamagnetic nanoparticles.

19. The method according to claim 12, wherein the isocyanate-reactive monomer A2
is selected from organic diols, organic diamines, organic polyalkylene glycols, organic polyether diols, organic polyesterdiols, polycarbonate diols, polyetherestercarbonate diols, or combinations thereof, and/or has a number average molecular weight Mn of from 400 g/mol to 2,500 g/mol and is selected from organic polyalkylene glycols, organic polyether diols, organic polyester diols or combinations thereof, and/or comprises a first isocyanate-reactive monomer A2a having two Zerewitinoff-reactive hydrogen atoms and a second isocyanate-reactive monomer A2b having three Zerewitinoff-reactive hydrogen atoms, whereby the first isocyanate-reactive monomer A2a is selected from compounds having two hydroxyl groups, amino groups, thiol groups, ketimine groups, ketazine groups, oxazolidine groups, or combinations thereof, and the second isocyanate-reactive monomer A2b is selected from compounds having three hydroxyl groups, amino groups, thiol groups, ketimine groups, ketazine groups, oxazolidine groups, or combinations thereof.

\* \* \* \* \*